(12) United States Patent
Hashimoto et al.

(10) Patent No.: US 9,524,551 B2
(45) Date of Patent: Dec. 20, 2016

(54) ULTRASOUND DIAGNOSIS APPARATUS AND IMAGE PROCESSING METHOD

(71) Applicant: TOSHIBA MEDICAL SYSTEMS CORPORATION, Otawara-shi (JP)

(72) Inventors: Shinichi Hashimoto, Otawara (JP); Tomoyuki Takeguchi, Minato (JP); Reiko Noda, Minato (JP); Taichiro Shiodera, Minato (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 15 days.

(21) Appl. No.: 14/637,096

(22) Filed: Mar. 3, 2015

(65) Prior Publication Data

US 2015/0178921 A1 Jun. 25, 2015

Related U.S. Application Data

(63) Continuation of application No. PCT/JP2013/073706, filed on Sep. 3, 2013.

(30) Foreign Application Priority Data

Sep. 3, 2012 (JP) .................. 2012-193045
Sep. 3, 2013 (JP) .................. 2013-182482

(51) Int. Cl.
*G06K 9/00* (2006.01)
*G06T 7/00* (2006.01)
*A61B 8/13* (2006.01)
*A61B 8/00* (2006.01)
*A61B 8/08* (2006.01)

(52) U.S. Cl.
CPC .............. *G06T 7/0016* (2013.01); *A61B 8/13* (2013.01); *A61B 8/463* (2013.01); *A61B 8/466* (2013.01);
(Continued)

(58) Field of Classification Search
CPC .................. G06T 7/0016; G06T 2207/10136; G06T 2207/20004; A61B 8/5207; A61B 8/463; A61B 8/483; A61B 8/13; A61B 8/523; A61B 8/5223; A61B 8/5261; A61B 8/4254; A61B 8/469
(Continued)

(56) References Cited

U.S. PATENT DOCUMENTS

2007/0010743 A1  1/2007  Arai
2010/0158332 A1* 6/2010  Rico .................... A61B 5/4312
                                          382/128
(Continued)

FOREIGN PATENT DOCUMENTS

JP   2007-195882 A   8/2007
JP   2004-105638 A   4/2008
(Continued)

OTHER PUBLICATIONS

International Search Report issued Oct. 8, 2013 for PCT/JP2013/073706 filed on Sep. 3, 2013 (with English translation).
(Continued)

*Primary Examiner* — Ali Bayat
(74) *Attorney, Agent, or Firm* — Oblon, McClelland, Maier & Neustadt, L.L.P.

(57) ABSTRACT

An ultrasound diagnosis apparatus according to an embodiment includes an extracting unit and a controlling unit. The extracting unit extracts, from a group of volume data, reference image data corresponding to ultrasound image data displayed on a display unit. The controlling unit causes the display unit to display the ultrasound image data and the reference image data. The extracting unit obtains information about an imaging region indicated by the ultrasound image data displayed on the display unit and sets a search
(Continued)

region for searching the reference image data from the group of volume data, on a basis of the obtained information.

14 Claims, 18 Drawing Sheets

(52) U.S. Cl.
CPC ............ *A61B 8/469* (2013.01); *A61B 8/5207* (2013.01); *A61B 8/5215* (2013.01); *A61B 8/5261* (2013.01); *G06T 2207/10136* (2013.01); *G06T 2207/20004* (2013.01)

(58) Field of Classification Search
USPC ........................................................ 382/131
See application file for complete search history.

(56) References Cited

U.S. PATENT DOCUMENTS

| | | | | |
|---|---|---|---|---|
| 2011/0060223 A1* | 3/2011 | Kim | .......................... | A61B 8/08 600/443 |
| 2011/0144500 A1 | 6/2011 | Nihei et al. | | |
| 2011/0150310 A1 | 6/2011 | Endo et al. | | |
| 2011/0224550 A1* | 9/2011 | Shinohara | ................ | A61B 8/00 600/443 |
| 2012/0310092 A1* | 12/2012 | Yawata | .................... | A61B 8/00 600/443 |
| 2014/0236001 A1* | 8/2014 | Kondou | ................... | A61B 8/14 600/424 |

FOREIGN PATENT DOCUMENTS

| | | |
|---|---|---|
| JP | 2011-83637 A | 4/2011 |
| JP | 2011-83638 A | 4/2011 |
| JP | 2011-125570 A | 6/2011 |
| JP | 2012-91042 A | 5/2012 |
| WO | WO 2009/136461 A1 | 11/2009 |
| WO | WO 2010/010782 A1 | 1/2010 |

OTHER PUBLICATIONS

International Written Opinion mailed on Oct. 8, 2013 for PCT/JP2013/073706 filed on Sep. 3, 2013.

* cited by examiner

REFERENCE VOLUME DATA (11)

ULTRASOUND DIAGNOSIS APPARATUS AND IMAGE PROCESSING METHOD

CROSS-REFERENCE TO RELATED APPLICATIONS

This application is a continuation of PCT international application Ser. No. PCT/JP2013/073706, filed on Sep. 3, 2013 which designates the United States, incorporated herein by reference, and which claims the benefit of priority from Japanese Patent Application No. 2012-193045, filed on Sep. 3, 2012 and Japanese Patent Application No. 2013-182482, filed on Sep. 3, 2013, the entire contents of which are incorporated herein by reference.

FIELD

Embodiments described herein relate generally to an ultrasound diagnosis apparatus and an image processing method.

BACKGROUND

Conventionally, ultrasound diagnosis apparatuses have widely been used in today's medicine, because of being more compact than other medical image diagnosis apparatuses such as X-ray Computed Tomography (CT) apparatuses and Magnetic Resonance Imaging (MRI) apparatuses and because of being capable of displaying, in a real-time manner, an image of the target of a medical examination such as the heart or the liver through a simple operation of applying an ultrasound probe to the body surface of an examined subject. However, because an ultrasound image has a smaller field-of-vision area than an X-ray CT image or an MRI image, it is difficult to understand the three-dimensional position and orientation of the observed site, and also, the quality of the image varies depending on the examined subject (hereinafter, "subject") and/or the person administering the medical examination.

To cope with this situation, in recent years, such an ultrasound diagnosis apparatus has been put into practical use that has a function of displaying an ultrasound image and another medical image (e.g., an X-ray CT image, an MRI image, or the like) taken on substantially the same cross-sectional plane as that of the ultrasound image, at the same time in a real-time manner. The ultrasound diagnosis apparatus generates, on a basis of position information of an ultrasound probe, the two-dimensional X-ray CT image or MRI image taken on substantially the same cross-sectional plane as the cross-sectional plane on which an ultrasound scan was performed, from X-ray CT volume data or MRI volume data, by performing a synchronized position alignment process on the positions of the images.

By using this function, for example, an operator is able to view, at the same time, the ultrasound image and the X-ray CT image taken on substantially the same cross-sectional plane as that of the ultrasound image. As a result, the operator is able to view the ultrasound image in a more comprehensible manner, in spite of ultrasound images generally having small field-of-vision areas, which make it difficult to understand the three-dimensional position of the observed site. For example, by viewing an X-ray CT image or an MRI image as a reference image at the same time with the ultrasound image, the operator is able to view a surrounding site in a wider area, the surrounding site not being depicted in the ultrasound image. As a result, the operator is able to recognize the three-dimensional position and orientation of the ultrasound image more easily. Furthermore, from the reference image, the operator is able to obtain morphological information of some parts that cannot be clearly recognized in the ultrasound image.

However, it is impossible to use the function described above, if the X-ray CT volume data or the MRI volume data of the subject who is subject to the ultrasound diagnosis process is not available.

DETAILED DESCRIPTION

An ultrasound diagnosis apparatus according to an embodiment includes an extracting unit and a controlling unit. The extracting unit extracts, from a group of volume data, reference image data corresponding to ultrasound image data displayed on a display unit. The controlling unit causes the display unit to display the ultrasound image data and the reference image data. The extracting unit obtains information about an imaging region indicated by the ultrasound image data displayed on the display unit and sets a search region for searching the reference image data from the group of volume data, on a basis of the obtained information.

Exemplary embodiments of an ultrasound diagnosis apparatus will be explained in detail below, with reference to the accompanying drawings.

First Embodiment

Figure 1:
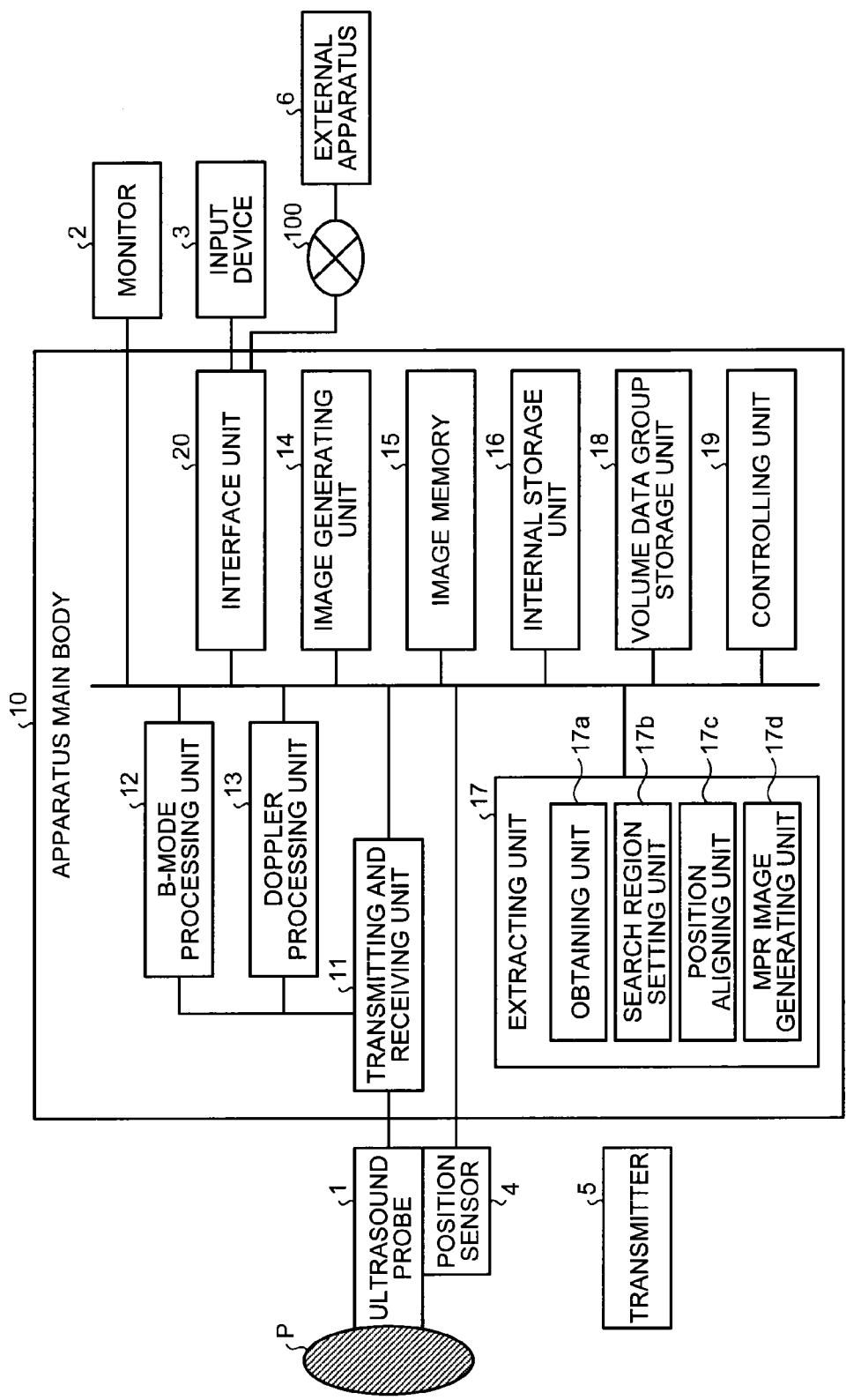
FIG. 1 is a block diagram of an exemplary configuration of an ultrasound diagnosis apparatus according to a first embodiment.

First, a configuration of an ultrasound diagnosis apparatus according to a first embodiment will be explained. FIG. 1 is a block diagram of an exemplary configuration of the ultrasound diagnosis apparatus according to the first embodiment. As shown in FIG. 1, the ultrasound diagnosis apparatus according to the first embodiment includes an ultrasound probe 1, a monitor 2, an input device 3, a position sensor 4, a transmitter 5, and an apparatus main body 10. Furthermore, the apparatus main body 10 is connected to an external apparatus 6 via a network 100.

The ultrasound probe 1 includes a plurality of transducer elements, which generate an ultrasound wave based on a drive signal supplied from a transmitting and receiving unit 11 included in the apparatus main body 10 (explained later). The transducer elements included in the ultrasound probe 1 are, for example, piezoelectric transducer elements. The ultrasound probe 1 receives a reflected-wave signal from an examined subject (hereinafter, "subject") P and converts the received reflected-wave signal into an electric signal. Furthermore, the ultrasound probe 1 includes matching layers included in the piezoelectric transducer elements, as well as a backing member that prevents ultrasound waves from propagating rearward from the piezoelectric transducer elements. The ultrasound probe 1 is detachably connected to the apparatus main body 10.

When an ultrasound wave is transmitted from the ultrasound probe 1 to the subject P, the transmitted ultrasound wave is repeatedly reflected on a surface of discontinuity of acoustic impedances at a tissue in the body of the subject P and is received as a reflected-wave signal by the plurality of piezoelectric transducer elements included in the ultrasound probe 1. The amplitude of the received reflected-wave signal is dependent on the difference between the acoustic impedances on the surface of discontinuity on which the ultrasound wave is reflected. When the transmitted ultrasound pulse is reflected on the surface of a flowing bloodstream or a cardiac wall, the reflected-wave signal is, due to the Doppler effect, subject to a frequency shift, depending on a velocity component of the moving members with respect to the ultrasound wave transmission direction.

For example, according to the first embodiment, to scan the subject P two-dimensionally, a one-dimensional (1D) array probe in which the plurality of piezoelectric transducer elements are arranged in a row is connected to the apparatus main body 10, as the ultrasound probe 1. For example, the 1D array probe serving as the ultrasound probe 1 may be a sector probe that performs a sector scan, a convex probe that performs an offset sector scan, or a linear probe that performs a linear scan.

Alternatively, in the first embodiment, for example, to scan the subject P three-dimensionally, a mechanical four-dimensional (4D) probe or a two-dimensional (2D) array probe may be connected to the apparatus main body 10, as the ultrasound probe 1. The mechanical 4D probe is able to perform a two-dimensional scan by employing a plurality of piezoelectric transducer elements arranged in a row like in a 1D array probe and is also able to perform a three-dimensional scan by causing the plurality of piezoelectric transducer elements to swing at a predetermined angle (a swinging angle). The 2D array probe is able to perform a three-dimensional scan by employing a plurality of piezoelectric transducer elements arranged in a matrix formation and is also able to perform a two-dimensional scan by transmitting ultrasound waves in a focused manner.

The position sensor 4 and the transmitter 5 are devices used for obtaining position information of the ultrasound probe 1. For example, the position sensor 4 may be configured with a magnetic sensor attached to the ultrasound probe 1. Furthermore, for example, the transmitter 5 may be configured with a device that is disposed in an arbitrary position and outwardly forms a magnetic field centered on itself.

The position sensor 4 detects the three-dimensional magnetic field formed by the transmitter 5. Furthermore, on a basis of information about the detected magnetic field, the position sensor 4 calculates the position thereof (coordinates and an angle) within a space in which the transmitter 5 is positioned at the origin and further transmits the calculated position to the apparatus main body 10. In this situation, the position sensor 4 transmits the three-dimensional coordinates and angle at which the position sensor 4 is located, to the apparatus main body 10, as three-dimensional position information of the ultrasound probe 1.

The first embodiment is also applicable to a situation where the position information of the ultrasound probe 1 is obtained by using a system other than the position detection system employing the position sensor 4 and the transmitter 5. For example, the first embodiment is also applicable to a situation where the position information of the ultrasound probe 1 is obtained by using a gyro sensor or an acceleration sensor.

The input device 3 is connected to the apparatus main body 10 via an interface unit 20 (explained later). The input device 3 includes a mouse, a keyboard, a button, a panel switch, a touch command screen, a foot switch, a trackball, and the like. The input device 3 receives various types of setting requests from an operator of the ultrasound diagnosis apparatus and transfers the received various types of setting requests to the apparatus main body 10.

The monitor 2 displays a Graphical User Interface (GUI) used by the operator of the ultrasound diagnosis apparatus to input the various types of setting requests through the input device 3 and displays ultrasound image data and the like generated by the apparatus main body 10.

The external apparatus 6 is an apparatus connected to the apparatus main body 10 via the interface unit 20 (explained later). For example, the external apparatus 6 may be configured with a database of a Picture Archiving and Communication System (PACS), which is a system that manages various types of medical image data, or may be configured with a database of an electronic medical record system that manages electronic medical records to which medical images are attached. Alternatively, the external apparatus 6 may be configured with any of various types of medical image diagnosis apparatuses (e.g., an X-ray Computed Tomography (CT) apparatus, a Magnetic Resonance Imaging (MRI) apparatus, or the like) other than the ultrasound diagnosis apparatus shown in FIG. 1.

From the external apparatus 6 via the interface unit 20, the apparatus main body 10 according to the first embodiment is able to obtain various types of medical image data that are uniformly put into an image format compliant with the Digital Imaging and Communications in Medicine (DICOM) specifications. For example, from the external apparatus 6 via the interface unit 20 (explained later), the apparatus main body 10 obtains reference-purpose volume data to be compared with the ultrasound image data generated by the ultrasound diagnosis apparatus. In this situation, the reference-purpose volume data is volume data taken by a medical image diagnosis apparatus other than the ultrasound diagnosis apparatus shown in FIG. 1. For example, the reference-purpose volume data is volume data taken by any of various types of medial image diagnosis apparatuses that are other than ultrasound diagnosis apparatuses.

The apparatus main body 10 is an apparatus that generates ultrasound image data based on the reflected-wave signal received by the ultrasound probe 1. The apparatus main body 10 shown in FIG. 1 is an apparatus that is able to generate two-dimensional ultrasound image data based on a two-dimensional reflected-wave signal and to be able to generate three-dimensional ultrasound image data based on a three-dimensional reflected-wave signal. However, the first embodiment is also applicable to a situation where the apparatus main body 10 is an apparatus exclusively for two-dimensional data.

As shown in FIG. 1, the apparatus main body 10 includes the transmitting and receiving unit 11, a B-mode processing unit 12, a Doppler processing unit 13, an image generating unit 14, an image memory 15, an internal storage unit 16, an extracting unit 17, a volume data group storage unit 18, a controlling unit 19, and the interface unit 20.

The transmitting and receiving unit 11 controls ultrasound transmissions and receptions performed by the ultrasound probe 1, on a basis of an instruction from the controlling unit 19 (explained later). The transmitting and receiving unit 11 includes a pulse generator, a transmission delaying unit, a pulser, and the like and supplies the drive signal to the ultrasound probe 1. The pulse generator repeatedly generates a rate pulse for forming a transmission ultrasound wave at a predetermined rate frequency. Furthermore, the transmission delaying unit applies a delay period that is required to focus the ultrasound wave generated by the ultrasound probe 1 into the form of a beam and to determine transmission directivity and that corresponds to each of the piezoelectric transducer elements, to each of the rate pulses generated by the pulse generator. Furthermore, the pulser applies a drive signal (a drive pulse) to the ultrasound probe 1 with timing based on the rate pulses. The transmission delaying unit arbitrarily adjusts the transmission directions of the ultrasound waves transmitted from the piezoelectric transducer element surfaces, by varying the delay periods applied to the rate pulses.

The transmitting and receiving unit 11 has a function to be able to instantly change the transmission frequency, the transmission drive voltage, and the like, for the purpose of executing a predetermined scanning sequence based on an instruction from the controlling unit 19 (explained later). In particular, the configuration to change the transmission drive voltage is realized by using a linear-amplifier-type oscillating circuit of which the value can be instantly switched or by using a mechanism that to electrically switches between a plurality of power source units.

The transmitting and receiving unit 11 includes a preamplifier, an Analog/Digital (A/D) converter, a reception delaying unit, an adder, and the like and generates reflected-wave data by performing various types of processes on the reflected-wave signal received by the ultrasound probe 1. The pre-amplifier amplifies the reflected-wave signal for each of channels. The A/D converter applies an A/D conversion to the amplified reflected-wave signal. The reception delaying unit applies a delay period required to determine reception directivity to the result of the A/D conversion. The adder performs an adding process on the reflected-wave signals processed by the reception delaying unit so as to generate the reflected-wave data. As a result of the adding process performed by the adder, reflected components from the direction corresponding to the reception directivity of the reflected-wave signals are emphasized. A comprehensive beam used in an ultrasound transmission/reception is thus formed according to the reception directivity and the transmission directivity.

When a two-dimensional scan is performed on the subject P, the transmitting and receiving unit 11 causes the ultrasound probe 1 to transmit two-dimensional ultrasound beams. The transmitting and receiving unit 11 then generates two-dimensional reflected-wave data from the two-dimensional reflected-wave signals received by the ultrasound probe 1. When a three-dimensional scan is performed on the subject P, the transmitting and receiving unit 11 causes the ultrasound probe 1 to transmit three-dimensional ultrasound beams. The transmitting and receiving unit 11 then generates three-dimensional reflected-wave data from the three-dimensional reflected-wave signals received by the ultrasound probe 1.

Output signals from the transmitting and receiving unit 11 can be in a form selected from various forms. For example, the output signals may be in the form of signals called Radio Frequency (RF) signals that contain phase information or may be in the form of amplitude information obtained after an envelope detection process.

The B-mode processing unit 12 and the Doppler processing unit 13 are signal processing units that performs various types of signal processing on the reflected-wave data generated by the transmitting and receiving unit 11 from the reflected-wave signals. The B-mode processing unit 12 receives the reflected-wave data from the transmitting and receiving unit 11 and generates data (B-mode data) in which the strength of each signal is expressed by a degree of brightness, by performing a logarithmic amplification, an envelope detection process, and the like on the received reflected-wave data. Furthermore, the Doppler processing unit 13 obtains velocity information from the reflected-wave data received from the transmitting and receiving unit 11 by performing a frequency analysis, and further generates data (Doppler data) obtained by extracting moving member information such as a velocity, a dispersion, a power, and the like that are under the influence of the Doppler effect, for a plurality of points. In this situation, the moving member may be, for example, the bloodstream, a tissue such as the cardiac wall, and/or a contrast agent.

The B-mode processing unit 12 and the Doppler processing unit 13 shown in FIG. 1 are able to process both two-dimensional reflected-wave data and three-dimensional reflected-wave data. In other words, the B-mode processing unit 12 is able to generate two-dimensional B-mode data from two-dimensional reflected-wave data and to generate three-dimensional B-mode data from three-dimensional reflected-wave data. The Doppler processing unit 13 is able to generate two-dimensional Doppler data from two-dimensional reflected-wave data and to generate three-dimensional Doppler data from three-dimensional reflected-wave data.

The image generating unit 14 generates ultrasound image data from the data generated by the B-mode processing unit 12 and the Doppler processing unit 13. In other words, from the two-dimensional B-mode data generated by the B-mode processing unit 12, the image generating unit 14 generates two-dimensional B-mode image data in which the strength of the reflected wave is expressed by a degree of brightness. Furthermore, from the two-dimensional Doppler data generated by the Doppler processing unit 13, the image generating unit 14 generates two-dimensional Doppler image data expressing moving member information. The two-dimensional Doppler image data is velocity image data, dispersion image data, power image data, or image data combining these types of image data.

In this situation, generally speaking, the image generating unit 14 converts (by performing a scan convert process) a scanning line signal sequence from an ultrasound scan into a scanning line signal sequence in a video format used by, for example, television and generates display-purpose ultrasound image data. More specifically, the image generating unit 14 generates the display-purpose ultrasound image data by performing a coordinate transformation process compliant with the ultrasound scanning mode used by the ultrasound probe 1. Furthermore, as various types of image processing other than the scan convert process, the image generating unit 14 performs, for example, an image processing (a smoothing processing) to re-generate a brightness-average image or an image processing (an edge enhancement processing) using a differential filter within images, while using a plurality of image frames obtained after the scan convert process is performed. Furthermore, the image generating unit 14 synthesizes additional information (text information of various parameters, scale graduations, body marks, and the like) with the ultrasound image data.

In other words, the B-mode data and the Doppler data are the ultrasound image data before the scan convert process is performed. The data generated by the image generating unit 14 is the display-purpose ultrasound image data obtained after the scan convert process is performed. The B-mode data and the Doppler data may also be referred to as raw data. The image generating unit 14 generates "two-dimensional B-mode image data or two-dimensional Doppler image data", which is display-purpose two-dimensional ultrasound image data, from "two-dimensional B-mode data or two-dimensional Doppler data", which is the two-dimensional ultrasound image data before the scan convert process is performed.

Furthermore, the image generating unit 14 generates three-dimensional B-mode image data by performing a coordinate transformation process on the three-dimensional B-mode data generated by the B-mode processing unit 12. Furthermore, the image generating unit 14 generates three-dimensional Doppler image data by performing a coordinate transformation process on the three-dimensional Doppler data generated by the Doppler processing unit 13. The image generating unit 14 generates "the three-dimensional B-mode image data or the three-dimensional Doppler image data" as "three-dimensional ultrasound image data (ultrasound volume data)".

Furthermore, the image generating unit 14 performs a rendering process on the volume data, to generate various types of two-dimensional image data used for displaying the volume data on the monitor 2. Examples of the rendering process performed by the image generating unit 14 include a process to generate Multi Planar Reconstruction (MPR) image data from the volume data by implementing an MPR method. Another example of the rendering process performed by the image generating unit 14 is Volume Rendering (VR) process to generate two-dimensional image data that reflects three-dimensional information.

Furthermore, the image generating unit 14 is able to perform the rendering process described above on volume data taken by another medical image diagnosis apparatus. The volume data may be three-dimensional X-ray CT image data (hereinafter, "X-ray CT volume data") taken by an X-ray CT apparatus or may be three-dimensional MRI image data (hereinafter, "MRI volume data") taken by an MRI apparatus. Furthermore, the image generating unit 14 is also able to perform the rendering process described above on ultrasound volume data taken by an ultrasound diagnosis apparatus other than the ultrasound diagnosis apparatus shown in FIG. 1.

The image memory 15 is a memory for storing therein the display-purpose image data generated by the image generating unit 14. Furthermore, the image memory 15 is also able to store therein the data generated by the B-mode processing unit 12 and the Doppler processing unit 13. After a diagnosis process, for example, the operator is able to invoke the B-mode data or the Doppler data stored in the image memory 15. The invoked data serves as the display-purpose ultrasound image data via the image generating unit 14. The image memory 15 also stores therein image data generated by the extracting unit 17 (explained later).

The internal storage unit 16 stores therein various types of data such as a control computer program (hereinafter, "control program") to realize ultrasound transmissions and receptions, image processing, and display processing, as well as diagnosis information (e.g., patients' IDs, medical doctors' observations), diagnosis protocols, and various types of body marks. Furthermore, the internal storage unit 16 may be used, as necessary, for storing therein any of the image data stored in the image memory 15. Furthermore, it is possible to transfer the data stored in the internal storage unit 16 to the external apparatus 6 via the interface unit 20 (explained later).

The extracting unit 17 is a processing unit that performs various types of processing on a group of volume data stored in the volume data group storage unit 18. As illustrated in FIG. 1, the extracting unit 17 includes an obtaining unit 17*a*, a search region setting unit 17*b*, a position aligning unit 17*c*, and an MPR image generating unit 17*d*. Processes performed by the extracting unit 17 while using the volume data group storage unit 18 will be explained in detail later.

The controlling unit 19 controls the entire processes performed by the ultrasound diagnosis apparatus. More specifically, based on the various types of setting requests input by the operator via the input device 3 and various types of control programs and various types of data read from the internal storage unit 16, the controlling unit 19 controls processes performed by the transmitting and receiving unit 11, the B-mode processing unit 12, the Doppler processing unit 13, the image generating unit 14, and the extracting unit 17. Furthermore, the controlling unit 19 exercises control so that the monitor 2 displays the display-purpose image data stored in the image memory 15 and the internal storage unit 16. Furthermore, the controlling unit 19 exercises control so that medical image data received from the operator via the input device 3 is transferred from the external apparatus 6 to the internal storage unit 16 or to the volume data group storage unit 18, via the network 100 and the interface unit 20.

The interface unit 20 is an interface for the input device 3, the network 100, and the external apparatus 6. The various types of setting information and the various types of instructions received from the operator by the input device 3 are transferred to the controlling unit 19 by the interface unit 20. For example, an image data transfer request received from the operator by the input device 3 is forwarded to the external apparatus 6 by the interface unit 20 via the network 100. Furthermore, image data transferred by the external apparatus 6 is stored into the internal storage unit 16 or into the volume data group storage unit 18 by the interface unit 20.

An overall configuration of the ultrasound diagnosis apparatus according to the first embodiment has thus been explained. The ultrasound diagnosis apparatus according to the first embodiment configured as described above is able to realize a "synchronized display function", which has been put into practical use in recent years. In other words, the ultrasound diagnosis apparatus according to the first embodiment is able to cause the image generating unit 14 to generate medical image data taken on substantially the same cross-sectional plane as that of a two-dimensional ultrasound scan performed for the purpose of generating two-dimensional ultrasound image data and is able to cause the monitor 2 to display the generated medical image data.

For example, before performing an ultrasound examination on the subject P by using the ultrasound probe 1, the operator makes a request that X-ray CT volume data of images taken at an examined site of the subject P should be transferred. Furthermore, the operator adjusts the position of a cross-sectional plane used for performing an MPR process via the input device 3, in such a manner that X-ray CT image data rendering the examined site of the subject P is displayed on the monitor 2.

Figure 2:
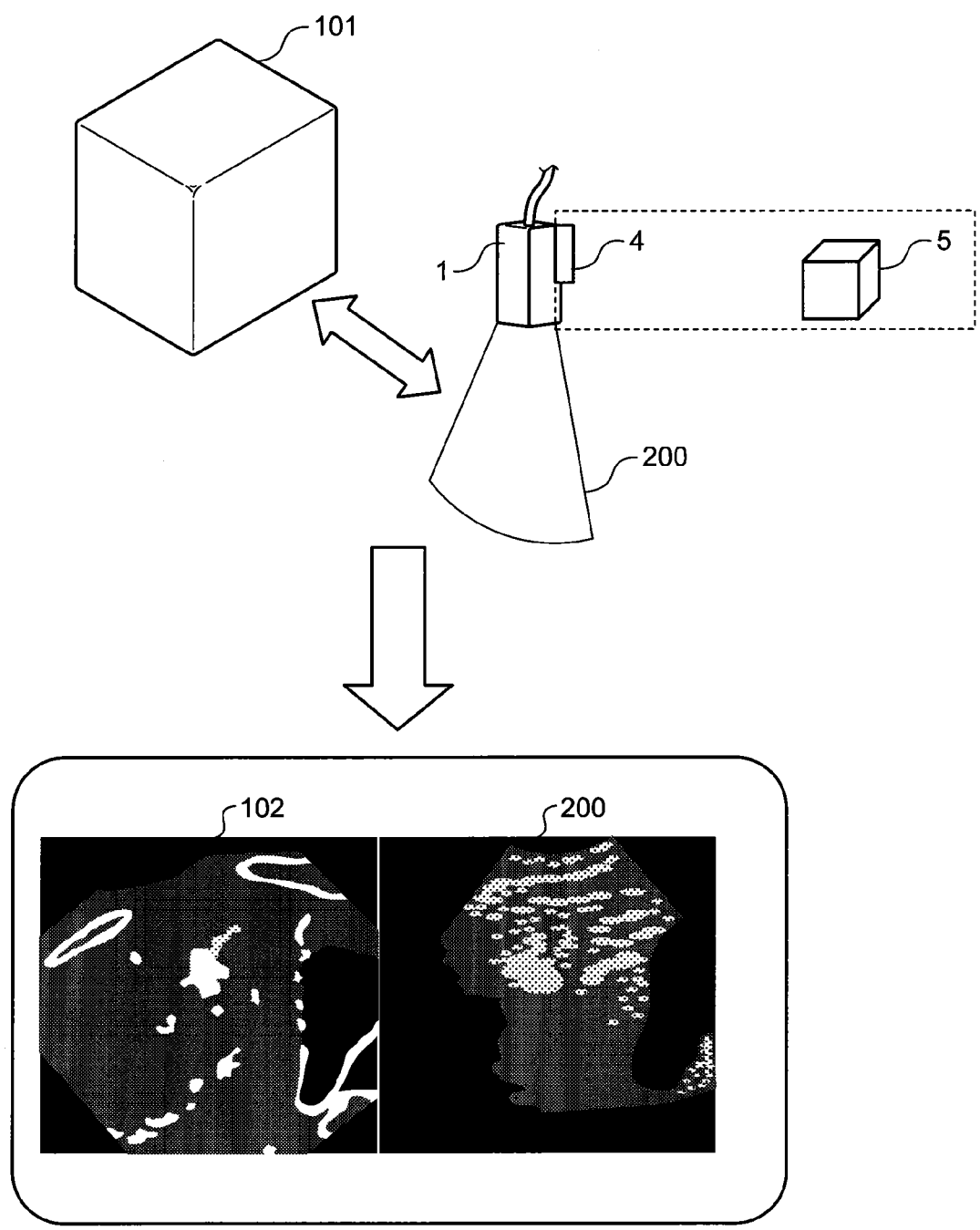
FIG. 2 is a drawing for explaining a conventional concurrent display function.

Furthermore, under control of the controlling unit 19, the image generating unit 14 generates X-ray CT image data obtained by cross-sectioning the X-ray CT volume data on the cross-sectional plane adjusted by the operator (hereinafter, an "initial cross-sectional plane"). The monitor 2 then displays the X-ray CT image data generated by the image generating unit 14. The operator operates the ultrasound probe 1 so that an ultrasound scan is performed on the same cross-sectional plane as that of the X-ray CT image data displayed on the monitor 2. When having determined that the X-ray CT image data displayed on the monitor 2 and the ultrasound image data are on substantially the same cross-sectional plane, the operator presses a "confirm" button included in the input device 3, for example. The controlling unit 19 sets three-dimensional position information of the ultrasound probe 1 obtained from the position sensor 4 at the point in time when the "confirm" button was pressed, to be initial position information. FIG. 2 is a drawing for explaining a conventional concurrent display function.

After that, the controlling unit 19 obtains three-dimensional position information of the ultrasound probe 1 corresponding to the time when ultrasound image data 200 shown in FIG. 2 was generated, from the position detection system including the position sensor 4 and the transmitter 5. Subsequently, the controlling unit 19 obtains movement information between the obtained three-dimensional position information and the initial position information and re-sets the cross-sectional plane for the MPR process, by changing the position of the initial cross-sectional plane on a basis of the obtained movement information. After that, under control of the controlling unit 19, the image generating unit 14 generates X-ray CT image data 102 from X-ray CT volume data 101 shown in FIG. 2, by using the cross-sectional plane that was re-set by the controlling unit 19. Subsequently, under control of the controlling unit 19, the monitor 2 displays the X-ray CT image data 102 and the ultrasound image data 200 side by side, as illustrated in FIG. 2.

By using the conventional concurrent display function described above, the operator is able to view, at the same time, the ultrasound image and the X-ray CT image taken on substantially the same cross-sectional plane as that of the ultrasound image, for example. Consequently, the operator is able to view the ultrasound image in a more comprehensible manner, in spite of ultrasound images generally having small field-of-vision areas, which make it difficult to understand the three-dimensional position of the observed site. However, it is impossible to use the conventional concurrent display function, if the X-ray CT volume data or the MRI volume data of the subject P who is subject to the ultrasound examination is not available.

To cope with this situation, according to the first embodiment, the extracting unit 17 illustrated in FIG. 1 performs a processing to display a reference-purpose image for the ultrasound image, even if no reference-purpose volume data of the subject P of whom the ultrasound image was taken is available. More specifically, the extracting unit 17 realizes a concurrent display function with the ultrasound image data of the subject P, by using a group of reference-purpose volume data of a person other than the subject P. In the following sections, the concurrent display function according to the first embodiment will be referred to as a "guide display function", so as to be differentiated from the conventional concurrent display function.

First, the volume data group storage unit 18 referred to by the extracting unit 17 has stored therein a group of volume data. The group of volume data stored in the volume data group storage unit 18 is a group of volume data taken by a medical image diagnosis apparatus. More specifically, the group of volume data stored in the volume data group storage unit 18 is a group of volume data taken by a medical image diagnosis apparatus other than the ultrasound diagnosis apparatus shown in FIG. 1. Even more specifically, the group of volume data stored in the volume data group storage unit 18 is a group of volume data taken by a medical image diagnosis apparatus of a type that is other than ultrasound diagnosis apparatuses. In this situation, the group of volume data stored in the volume data group storage unit 18 is a group of volume data of an arbitrary subject. In the first embodiment, the group of volume data is a group of volume data of an arbitrary subject taken by a medical image diagnosis apparatus of a type that is other than ultrasound diagnosis apparatuses. In other words, the group of volume data includes a group of volume data of the subject other than the subject P who is subject to the ultrasound examination and is a group of reference-purpose volume data used for generating reference image data to be viewed at the same time with the ultrasound image data of the subject P.

In the following sections, an example will be explained in which the group of volume data stored in the volume data group storage unit 18 is a group of X-ray CT volume data of a subject other than the subject P. The group of X-ray CT volume data, which serves as a group of reference volume data, is stored into the volume data group storage unit 18 from the external apparatus 6, via the interface unit 20, for example. The first embodiment is also applicable to a situation where the group of reference-purpose volume data is a group of MRI volume data or a mixture of both a group of X-ray CT volume data and a group of MRI volume data. Furthermore, the first embodiment is also applicable to a situation where the volume data group storage unit 18 is a database of any of various types that is connected to the apparatus main body as the external apparatus 6.

Figure 3:
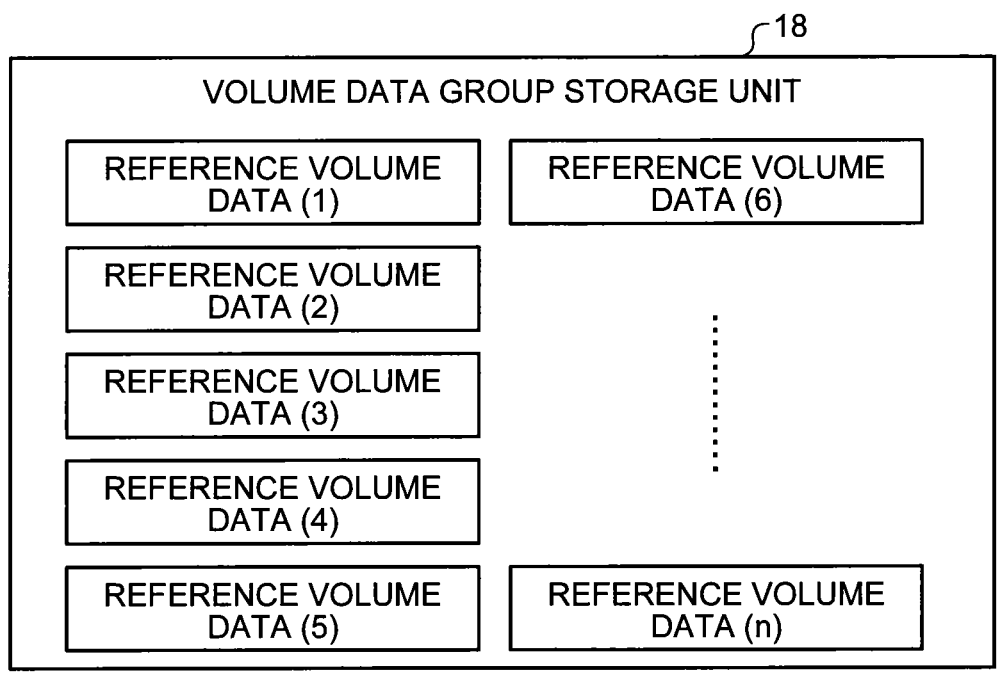
FIG. 3 is a drawing of an example of a volume data group storage unit.

FIG. 3 is a drawing of an example of the volume data group storage unit. For example, as illustrated in FIG. 3, the volume data group storage unit 18 stores therein "reference volume data (1) to reference volume data (n)", as a group of reference volume data. These pieces of reference volume data may be X-ray CT volume data obtained by taking images of the entire body of the subject or may be X-ray CT volume data obtained by taking images of a specific site. In this situation, although not shown in FIG. 3, the volume data group storage unit 18 stores therein additional information of the pieces of reference volume data.

As an example, if the reference volume data is X-ray CT volume data obtained by taking images of the "upper abdomen", the volume data group storage unit 18 stores therein "image taking region: upper abdomen" as additional information of the reference volume data. In another example, if the reference volume data is X-ray CT volume data obtained by taking images of the entire body of the subject, the volume data group storage unit 18 stores therein "the coordinates of a region corresponding to the neck" and "the coordinates of a region corresponding to the chest" as additional information of the reference volume data. By referring to the additional information, the extracting unit 17 is able to set a region corresponding to the "chest" within the X-ray CT volume data of the entire body, for example. Alternatively, the volume data group storage unit 18 may store therein position information (coordinates) of an organ (e.g., the heart in the chest, or the liver in the upper abdomen) included in the reference volume data, as additional information. For example, the position information can be obtained by an apparatus having a segmentation processing function, through a processing performed on the reference volume data. By referring to the additional information, the extracting unit 17 is able to set a region corresponding to the "heart" within X-ray CT volume data of the chest, for example.

Furthermore, the volume data group storage unit 18 stores therein information about the posture of the subject (the subject other than the subject P) during the image taking processing, as additional information of the pieces of reference volume data. The posture information is used for, for example, identifying an axial plane, a coronal plane, a sagittal plane, and the body axis direction of the subject, for the reference volume data. Furthermore, the volume data group storage unit 18 stores therein information that keeps the voxel size of the volume data in correspondence with the size of the real space, as additional information of the pieces of reference volume data. The size correspondence information is used for, for example, scaling the ultrasound image data and the reference volume data. Furthermore, the volume data group storage unit 18 may store therein information about the body (e.g., the height, the weight, and the physique) of the subject in the reference volume data, as additional information of the pieces of reference volume data.

Furthermore, the extracting unit 17 extracts a piece of reference image data corresponding to the ultrasound image data displayed on the monitor 2, from the group of reference volume data stored in the volume data group storage unit 18. In other words, the extracting unit 17 extracts the piece of reference image data similar to the ultrasound image data displayed on the monitor 2, from the group of reference volume data of the arbitrary subject stored in the volume data group storage unit 18. The volume data from which the reference image data is extracted is volume data of the arbitrary subject taken by a medical image diagnosis apparatus. More specifically, the volume data from which the reference image data is extracted is the volume data of the arbitrary subject taken by the medical image diagnosis apparatus of a type that is other than ultrasound diagnosis apparatuses. Even more specifically, the volume data from which the reference image data is extracted is volume data (e.g., X-ray CT volume data) of the subject other than the subject P taken by the medical image diagnosis apparatus of a type that is other than ultrasound diagnosis apparatuses. In other words, the volume data from which the reference image data is extracted is the volume data (e.g., X-ray CT volume data or MRI volume data) of the subject other than the subject P who is the image taking target of the ultrasound image data displayed on the monitor 2.

First, the obtaining unit 17a included in the extracting unit 17 obtains information about an imaging region indicated by the ultrasound image data displayed on the monitor 2. After that, the search region setting unit 17b included in the extracting unit 17 sets a search region for searching the reference image data from the group of reference volume data, on a basis of the information obtained by the obtaining unit 17a.

More specifically, the obtaining unit 17a according to the first embodiment obtains the position information of the ultrasound probe 1, from the position detection system employing the position sensor 4 and the transmitter 5. After that, the search region setting unit 17b (or the obtaining unit 17a) according to the first embodiment obtains the information about the imaging region, on a basis of position information of the ultrasound probe 1 corresponding to a time when the ultrasound image data was generated. Furthermore, the search region setting unit 17b according to the first embodiment sets the search region on a basis of the information about the imaging region. In other words, the search region setting unit 17b narrows down the area for searching the reference image data from the group of reference volume data, on a basis of the information about the imaging region.

Figure 4:
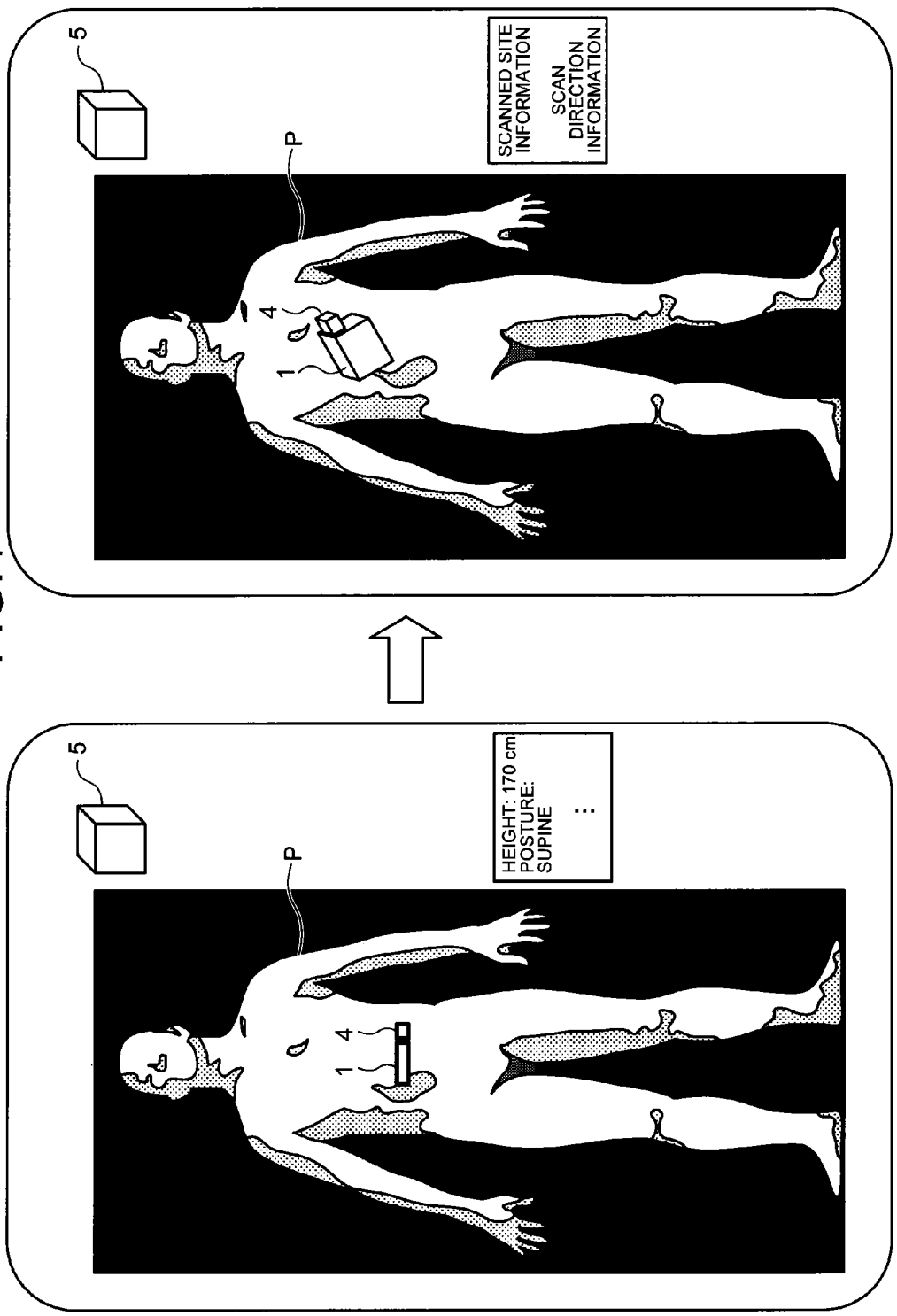
FIG. 4 is a drawing for explaining an example of a process performed by an obtaining unit according to the first embodiment.

The obtaining unit 17a according to the first embodiment will be explained, with reference to FIG. 4. FIG. 4 is a drawing for explaining an example of a processing performed by the obtaining unit according to the first embodiment.

Like the conventional concurrent display function, the guide display function according to the first embodiment uses the position detection system employing the position sensor 4 and the transmitter 5. In this regard, in the first embodiment, a function which the position detection system is required to have is, at least, to detect in what position on the body surface of the subject P, the ultrasound probe 1 is abutting against the subject P.

To realize this function, the operator at first causes the ultrasound probe 1 having the position sensor 4 attached thereto to abut against the subject P in a position that is set in advance, in a predetermined direction. For example, as illustrated on the left side of FIG. 4, the operator causes the ultrasound probe 1 having the position sensor 4 attached thereto to abut against the navel of the subject P and, furthermore, in such a direction that the ultrasound probe 1 scans an axial plane of the subject P.

Furthermore, the operator inputs body information of the subject P by using the input device 3. For example, as illustrated on the left side of FIG. 4, the operator inputs body information indicating that the height of the subject P is "170 centimeters", whereas the posture of the subject P lying on the bed is "supine". Furthermore, although not shown, as body information of the subject P, the operator either inputs or selects body orientation information indicating that the head of the subject P is positioned near the transmitter 5, whereas the legs of the subject P are positioned away from the transmitter 5. Furthermore, although not shown, as body information of the subject P, the operator inputs information used for identifying in what position (the distance and the direction) each of the body parts (e.g., the head, the neck, the chest, the right arm, the left arm, the upper abdomen, the lower abdomen, the upper legs, and the lower legs) of the subject P is located with respect to the navel. The inputs of the body information may be realized with a variety of other methods, such as selecting from ethnic group information and/or from average-value data or inputting a measured value. Furthermore, for example, the weight of the subject and/or physique information (e.g., underweight, normal, overweight, or obese) may be input as body information. By using the physique information, it is possible to further narrow down the search region in the processing performed at a subsequent stage.

A registration of initial information for realizing the guide display function has thus been completed. The obtaining unit 17a obtains position information of the ultrasound probe 1 corresponding to the point in time when the initial information was registered. The position information is information indicating the coordinates at the body surface where the navel of the subject P is located and the orientation (the angle) of the axial plane of the subject P.

After the initial information has been registered, as illustrated on the right side of FIG. 4, the operator moves the ultrasound probe 1 from the initial position and scans an examined site. After that, for example, at a point in time when the operator has determined that the ultrasound image data displayed on the monitor 2 is an image rendering the examined site, the operator presses a "guide display function start button" included in the input device 3.

When having received a guide display function start request, the obtaining unit 17a obtains position information of the ultrasound probe 1 corresponding to the time when the ultrasound image data displayed on the monitor 2 was generated. More specifically, as illustrated on the right side of FIG. 4, the obtaining unit 17a obtains scanned site information and scan direction information of the ultrasound image data, on a basis of the position information (the coordinates and the angle) transmitted by the position sensor 4. For example, the obtaining unit 17a obtains, as the scanned site information, a moving distance and a moving direction of the ultrasound probe 1 calculated from the coordinates of the scanned site of the ultrasound image data and the coordinates in the initial information. Furthermore, for example, the obtaining unit 17a obtains, as the scan direction information, an inclination of the ultrasound probe 1 calculated from the scan direction of the ultrasound image data and the orientation in the initial information.

Figure 5:
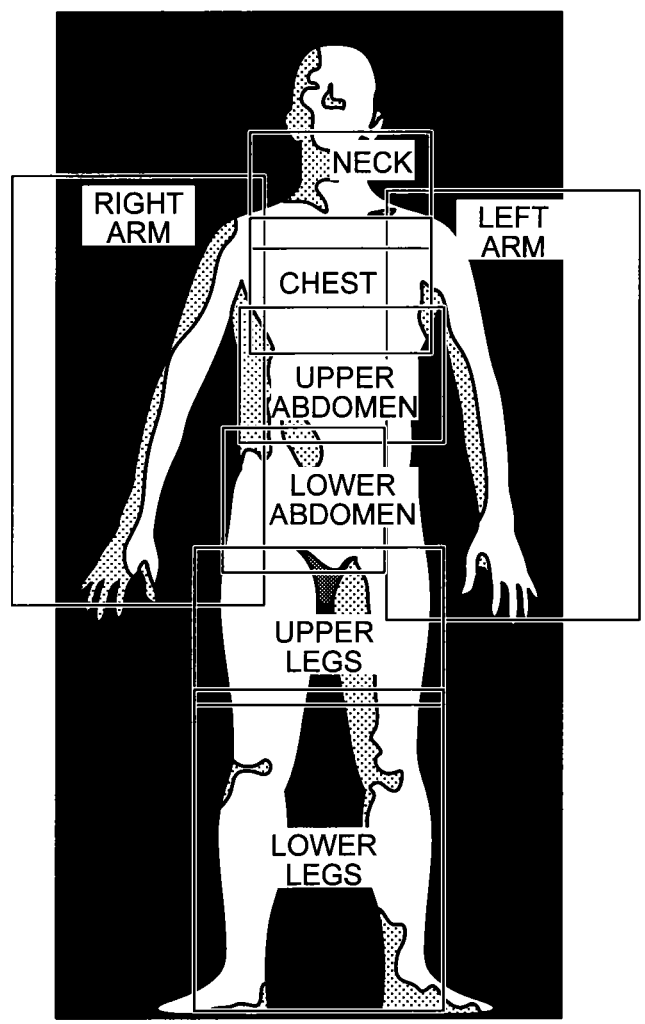
FIG. 5, FIG. 6 and FIG. 7 are drawings for explaining a search region setting unit according to the first embodiment.
Figure 6:
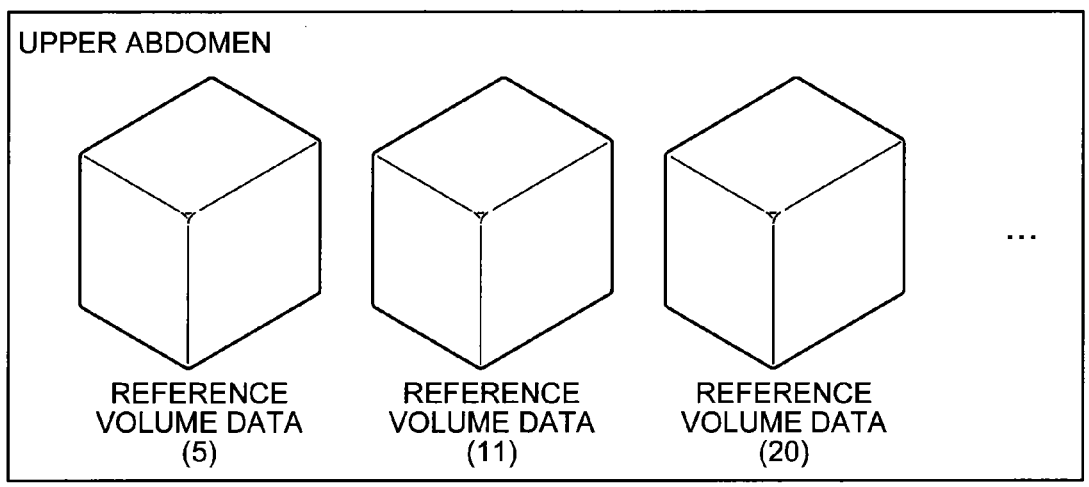
Figure 7:
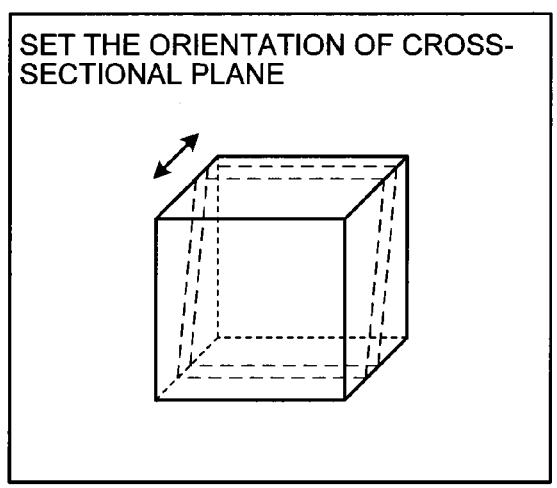

Furthermore, the search region setting unit 17b sets (narrows down) a search region. FIGS. 5 to 7 are drawings for explaining the search region setting unit according to the first embodiment. For example, as illustrated in FIG. 5, the search region setting unit 17b determines which one of the following sites corresponds to the imaging region indicated by the ultrasound image data, on a basis of the scanned site information obtained by the obtaining unit 17a: "the head, the neck, the chest, the right arm, the left arm, the upper abdomen, the lower abdomen, the upper legs, and the lower legs".

For example, on a basis of the scanned site information and the body information of the subject P, the search region setting unit 17b determines that the imaging region is the upper abdomen. In that situation, the search region setting unit 17b selects reference volume data corresponding to the "upper abdomen" from the group of reference volume data. For example, as illustrated in FIG. 6, the search region setting unit 17b selects "reference volume data (5), reference volume data (11), reference volume data (20) . . . " from the group of reference volume data. In this manner, as a search region setting processing, the search region setting unit 17b narrows down the reference volume data including the imaging region indicated by the ultrasound image data, to volume data from which the reference image data is to be searched for.

In other words, the imaging region kept in correspondence with each piece of reference volume data is defined on a basis of the imaging region determined by the search region setting unit 17b. Furthermore, each of the pieces of reference volume data may be a piece of volume data overlapping with a plurality of sites. The definition of the imaging regions illustrated in FIG. 5 is merely an example; it is also acceptable to define the imaging regions with more detailed regions. Furthermore, the search region setting unit 17b is able to narrow down the reference volume data, on a basis of the body information (i.e., the information about the height, the physique, and the like) of the subject P described above. For example, the search region setting unit 17b obtains the body information of the reference volume data together with the imaging region, from the additional information of the pieces of reference volume data. Furthermore, for example, from among "reference volume data (5), reference volume data (11), reference volume data (20) . . . " illustrated in FIG. 6, the search region setting unit 17b selects one or more pieces of reference volume data to which additional information including body information that is similar to the body information of the subject P is attached. Furthermore, on a basis of the scanned site information and the body information of the subject P, the search region setting unit 17b may determine the organ of which the images were taken and may further narrow down the search region in the reference volume data that has been narrowed down by the processing described above. For example, the search region setting unit 17b determines that the organ of which the images were taken was the "liver", on a basis of the scanned site information and the body information of the subject P. In that situation, for example, the search region setting unit 17b obtains a region corresponding to the "liver" from each of the pieces of reference volume data, namely "reference volume data (5), reference volume data (11), reference volume data (20) . . . " illustrated in FIG. 6, on a basis of the additional information of the pieces of volume data and sets the obtained regions as search regions. In other words, as a search region setting processing, the search region setting unit 17b may set the region for searching the reference image data from the reference volume data selected based on the imaging region, on a basis of the organ rendered in the ultrasound image data.

Furthermore, for example, as illustrated in FIG. 7, the search region setting unit 17b sets the orientation of the cross-sectional planes used for cross-sectioning the reference volume data, on a basis of the scan direction information obtained by the obtaining unit 17a. For example, the search region setting unit 17b sets the orientations of a plurality of cross-sectional planes used for generating MPR image data obtained by cross-sectioning "reference volume data (5), reference volume data (11), reference volume data (20) . . . ", on a basis of the scan direction information. In other words, as a search region setting processing, the search region setting unit 17b sets the cross-sectional plane orientations that are used for searching for the reference image data from the pieces of reference volume data that have been narrowed down, on a basis of the position information of the ultrasound probe 1. Furthermore, as a search region setting processing, the search region setting unit 17b may further set cross-sectional plane orientations and cross-sectional areas used for searching for the reference image data from pieces of volume data, on a basis of the position information of the ultrasound probe 1 and field-of-vision area information of the ultrasound image data. In this situation, the field-of-vision area information of the ultrasound image data is "depth information of the ultrasound image data" or "the angle of view" that can be obtained from ultrasound transmission/reception conditions. The search region setting unit 17b is able to obtain a scan form of the ultrasound image data by using the field-of-vision area information. For example, the search region setting unit 17b obtains the field-of-vision area information from the controlling unit 19. Furthermore, the search region setting unit 17b is able to set an area corresponding to the scan form of the ultrasound image data obtained from the field-of-vision area information on a cross-sectional plane obtained by cross-sectioning the reference volume data according to the cross-sectional plane orientation that was set, as a cross-sectional area for searching the reference image data.

Furthermore, although not shown, the search region setting unit 17b further sets a direction corresponding to the depth direction of the ultrasound image data on the cross-sectional plane of the reference volume data, on a basis of the additional information (the posture) of the reference volume data and the scan direction information. The search region setting unit 17b performs the search region setting processing on a basis of at least one type of information selected from the following: the imaging region, the body information, the image taking organ, the position information of the ultrasound probe 1, and the field-of-vision area information of the ultrasound image data.

After that, the position aligning unit 17c included in the extracting unit 17 aligns positions of the ultrasound image data and the group of volume data in the search region through a pattern matching processing. In other words, the position aligning unit 17c according to the first embodiment identifies the cross-sectional plane used for generating and extracting reference image data similar to the ultrasound image data from the reference volume data, by performing the position alignment processing.

In this situation, as a result of the setting processing performed by the search region setting unit 17b described above, the reference volume data in the region including the imaging region indicated by the ultrasound image data has been selected, and furthermore, the orientations of the cross-sectional planes (the cross-sectional plane orientations) in the selected pieces of reference volume data to be used for the MPR process have been set. For this reason, the position aligning unit 17c according to the first embodiment performs the pattern matching processing between pieces of two-dimensional image data. If the cross-sectional areas as described above are also set together with the cross-sectional plane orientations, the position aligning unit 17c sets the shapes and the sizes of the areas on which the pattern matching processing between the pieces of two-dimensional image data is to be performed, by using the cross-sectional areas.

For example, the position aligning unit 17c causes the MPR image generating unit 17d to cross-section each of the pieces of reference volume data, namely "reference volume data (5), reference volume data (11), reference volume data (20) . . . ", at the plurality of cross-sectional planes in the orientations set by the search region setting unit 17b. As a result, a plurality of pieces of MPR image data are generated as a group of candidate image data for the reference image data.

In this situation, the directions corresponding to the lateral direction and the depth direction of the ultrasound image data are identified in each of the pieces of candidate image data structuring the group of candidate image data. Furthermore, the pixel sizes of the pieces of candidate image data structuring the group of candidate image data and the ultrasound image data are scaled according to the additional information of the pieces of reference volume data described above.

In this situation, the position aligning unit 17c identifies the cross-sectional plane corresponding to the ultrasound image data by using a publicly-known method for performing the position alignment processing. For example, according to an instruction from the position aligning unit 17c, the image generating unit 14 generates image data by performing a smoothing processing (a spatial averaging processing) on the image data obtained by narrowing the dynamic range of brightness information of the ultrasound image data displayed on the monitor 2. The generated image data is such image data in which information about the tissue formation is patterned (hereinafter, "ultrasound formation pattern data"). Furthermore, according to an instruction from the position aligning unit 17c, the image generating unit 14 also performs a similar processing on the pieces of candidate image data, so as to generate image data in which information about the tissue formation is patterned (hereinafter, "CT formation pattern data"). After that, for example, the position aligning unit 17c performs a brightness inversion processing and various types of size-adjusting process (fine-tuning the overall size) on the CT formation pattern data and determines a level of similarity between the two types of formation pattern data, by using a cross-correlation, an auto-correlation, a mutual information value, a normalized mutual information value, a correlation ratio, or the like.

For example, by judging a level of similarity between the entirety of the ultrasound formation pattern data and each of the pieces of CT formation pattern data, the position aligning unit 17c narrows down the pieces of CT formation pattern data to a number of pieces of CT formation pattern data that are similar to the ultrasound formation pattern data. Furthermore, for example, the position aligning unit 17c divides the narrowed-down pieces of CT formation pattern data and the ultrasound formation pattern data into a plurality of mesh sections, so as to judge levels of similarity between corresponding mesh sections. Furthermore, for example, the position aligning unit 17c selects the piece of CT formation pattern data having the largest sum of similarity levels and further identifies the position of the cross-sectional plane of the candidate image data from which the selected piece of CT formation pattern data was generated.

In this situation, when judging the levels of similarity, the position aligning unit 17c may select a piece of CT formation pattern data having the highest level of similarity, after fine-tuning the orientations of the cross-sectional planes that are set.

Figure 8:
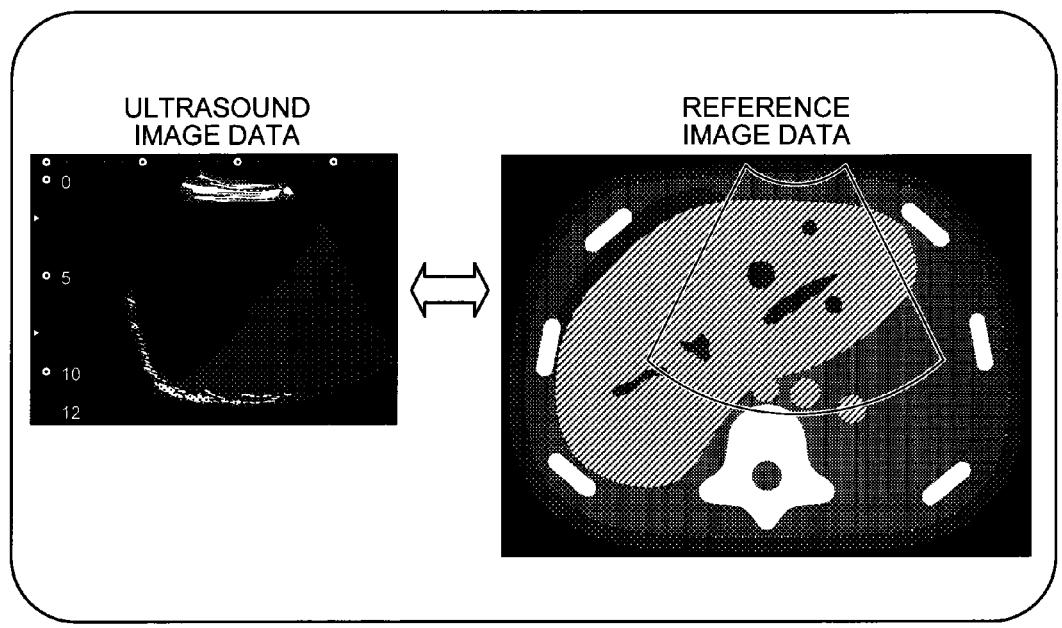
FIG. 8 is a drawing of an example of reference image data.

After that, the MPR image generating unit 17d generates MPR image data by cross-sectioning the reference volume data where the piece of CT formation pattern data having the highest level of similarity was selected, on the cross-sectional plane identified by the position aligning unit 17c, and stores the generated MPR image data into the image memory 15. FIG. 8 is a drawing of an example of the reference image data. The MPR image data is, as illustrated in FIG. 8, reference image data similar to the ultrasound image data. In this situation, as illustrated in FIG. 8, the MPR image generating unit 17d is able to draw a border indicating an area within the reference image data corresponding to the ultrasound image data, on a basis of the processing result by the position aligning unit 17c.

Alternatively, the first embodiment may be configured so that the processing performed by the MPR image generating unit 17*d* is performed by the image generating unit 14. Furthermore, the first embodiment is also applicable to a situation where the search region setting unit 17*b* narrows down only the imaging region. In that situation, the position aligning unit 17*c* identifies the cross-sectional plane used for generating the reference image data, by using a group of candidate image data obtained by cross-sectioning the reference image data of the region including the imaging region indicated by the ultrasound image data, on cross-sectional planes in a plurality of orientations. Furthermore, in that situation, the position aligning unit 17*c* may perform a patter matching processing between the pieces of reference volume data of the region including the imaging region indicated by the ultrasound image data and the two-dimensional ultrasound image data.

Figure 9:
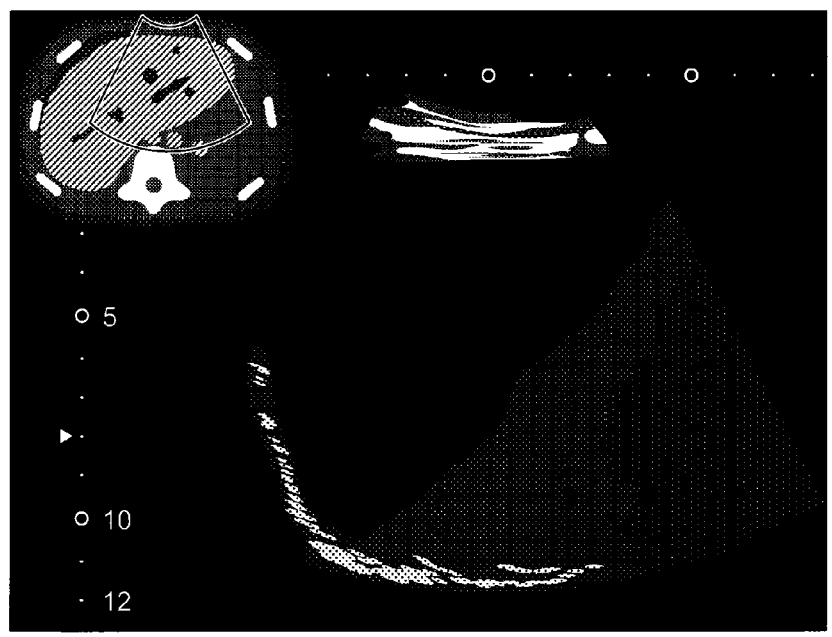
FIG. 9 and FIG. 10 are drawings of an example of a guide display screen.
Figure 10:
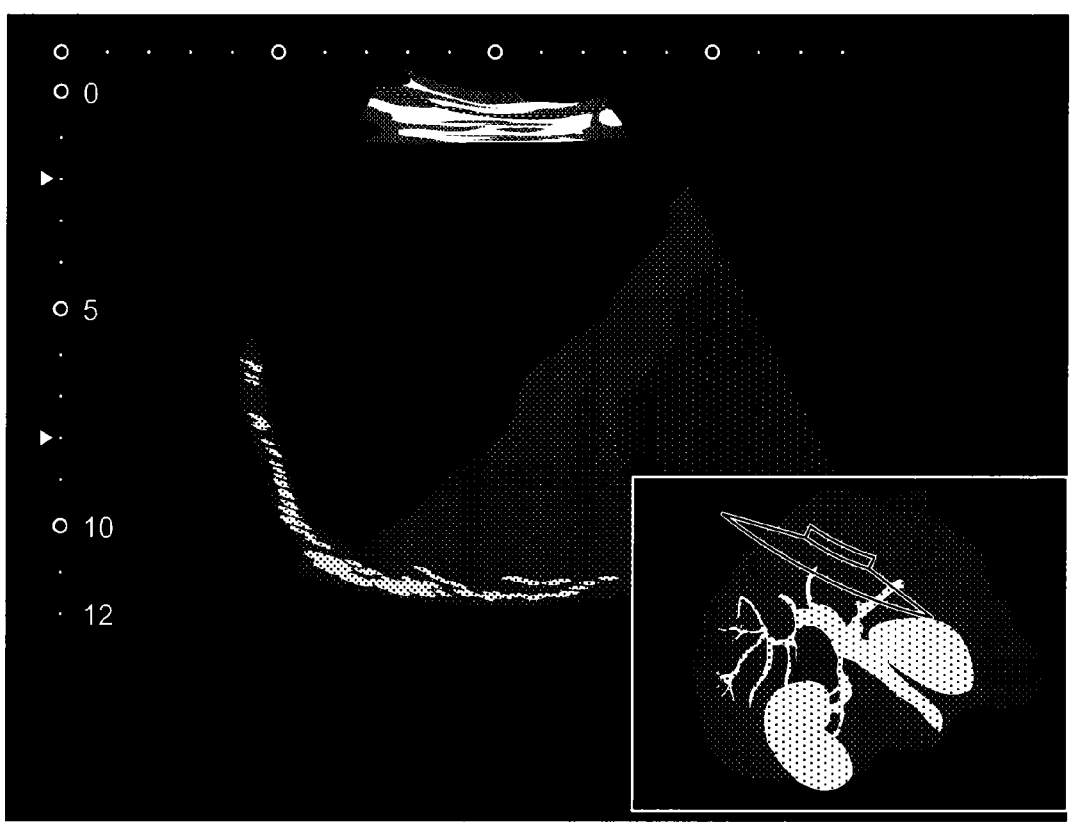

The controlling unit 19 causes the monitor 2 to display the ultrasound image data and the reference image data. FIGS. 9 and 10 are drawings of examples of guide display screens.

For example, under control of the controlling unit 19, the monitor 2 displays the ultrasound image data and the reference image data, as illustrated in FIG. 9. On the guide display screen illustrated in FIG. 9, reference image data having a border superimposed thereon to indicate the area corresponding to the ultrasound image data is displayed in the top left corner of the ultrasound image data.

Alternatively, instead of causing the reference image data itself to be displayed, the controlling unit 19 may cause such image data to be displayed in which, for example, a schematic drawing of the scanned region of the ultrasound image data is superimposed on volume rendering image data of reference volume data (11) from which the reference image data was extracted. On the guide display screen illustrated in FIG. 10, image data obtained by superimposing a schematic drawing on volume rendering image data is displayed in the bottom right corner of the ultrasound image data.

Figure 11:
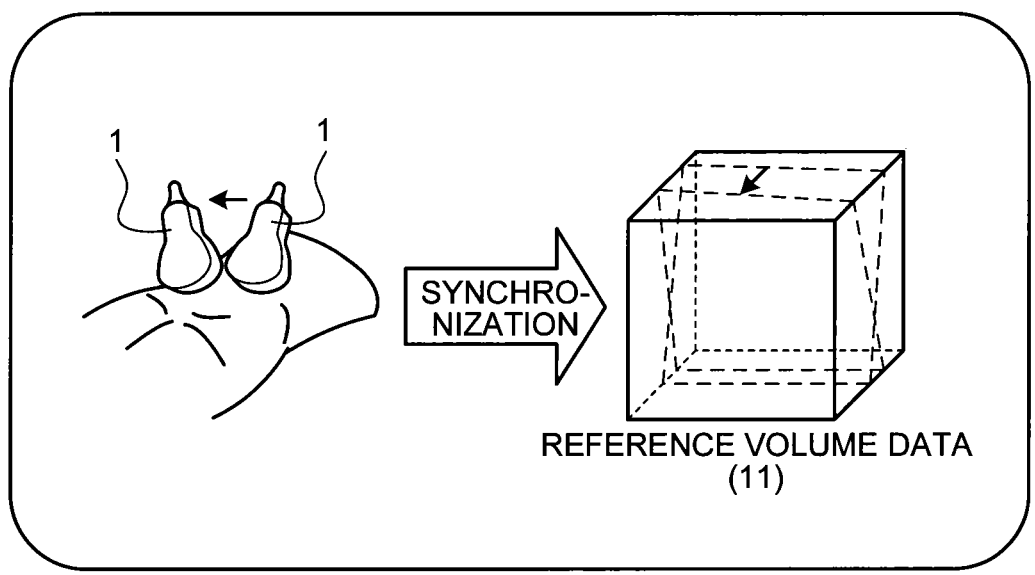
FIG. 11 is a drawing for explaining a tracking synchronization of a guide display function.

After that, in conjunction with an update of the ultrasound image data, the extracting unit 17 performs a processing of extracting reference image data again. In other words, according to the first embodiment in which the position detection system is used, after the cross-sectional plane corresponding to the ultrasound image data is identified by performing the pattern matching processing, the extracting unit 17 moves the cross-sectional plane or the reference image data, by realizing a tracking synchronization with changes in the position information of the ultrasound probe 1, like in the conventional synchronized display function. FIG. 11 is a drawing for explaining the tracking synchronization realized by the guide display function.

For example, as illustrated in FIG. 11, when the position information of the ultrasound probe 1 obtained by the obtaining unit 17*a* has changed, the position aligning unit 17*c* updates the cross-sectional plane in reference volume data (11), in accordance with the change amount of the position information.

Figure 12:
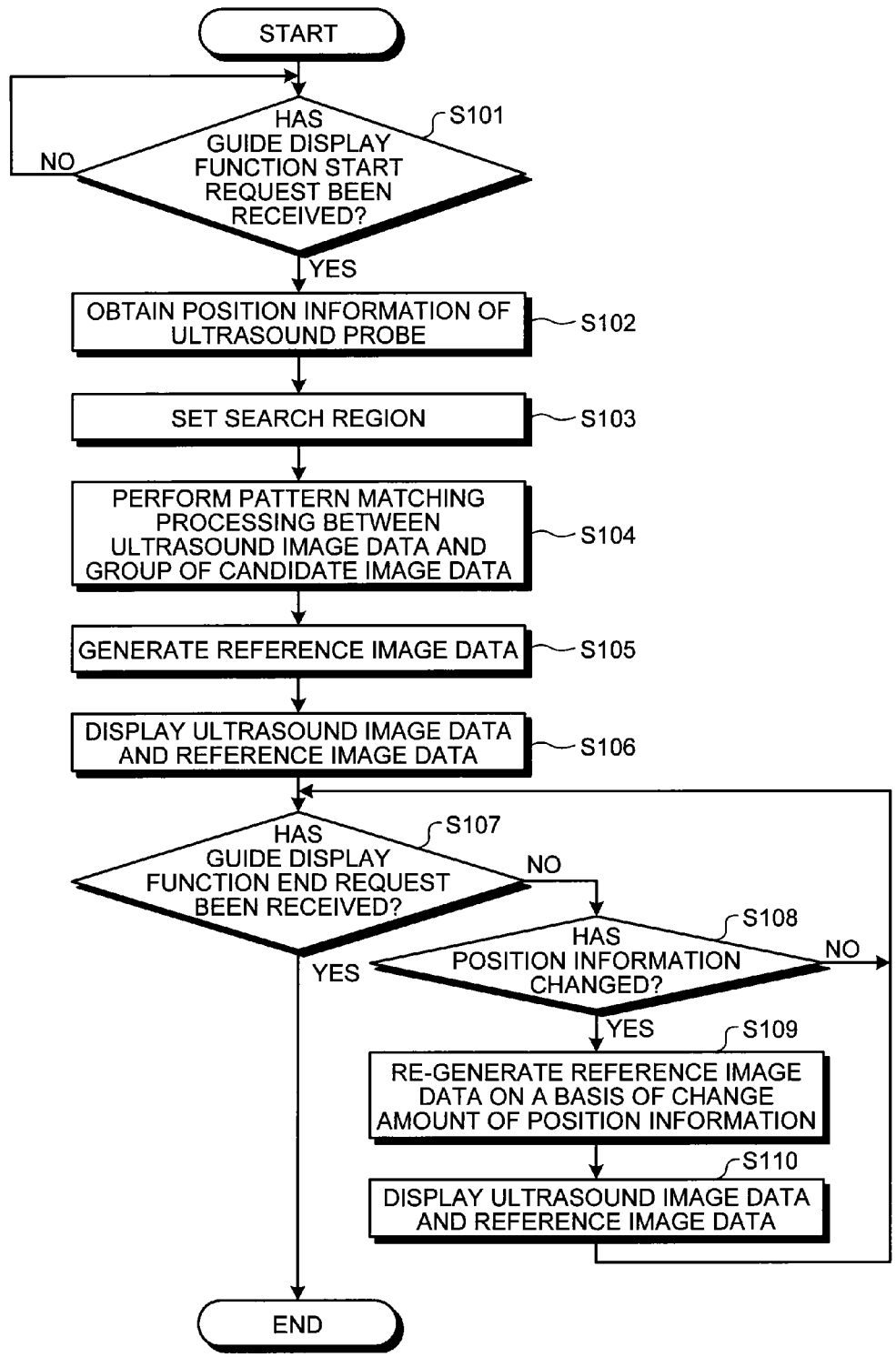
FIG. 12 is a flowchart for explaining a guide display function realized by the ultrasound diagnosis apparatus according to the first embodiment.

Next, an example of a processing of the guide display function realized by the ultrasound diagnosis apparatus according to the first embodiment will be explained, with reference to FIG. 12. FIG. 12 is a flowchart for explaining the guide display function realized by the ultrasound diagnosis apparatus according to the first embodiment. The example illustrated in FIG. 12 explains a processing that is performed after the registration of the initial information for realizing the guide display function has been completed, and also, the ultrasound probe 1 has been moved from the initial position so as to scan an examined site.

As illustrated in FIG. 12, the controlling unit 19 of the ultrasound diagnosis apparatus according to the first embodiment judges whether a guide display function start request has been received (step S101). If no start request has been received (step S101: No), the controlling unit 19 stands by until a start request is received.

On the contrary, if a guide display function start request has been received (step S101: Yes), the obtaining unit 17*a* obtains the position information of the ultrasound probe 1 at the current point in time (step S102), and the search region setting unit 17*b* sets a search region in the group of reference volume data (step S103). After that, the position aligning unit 17*c* performs a pattern matching processing between the ultrasound image data and a group of candidate image data (step S104). The position aligning unit 17*c* selects, by performing a pattern matching processing, the piece of candidate image data having the highest level of similarity to the ultrasound image data and identifies the position of the cross-sectional plane of the selected piece of candidate image data in the reference volume data.

After that, the MPR image generating unit 17*d* generates reference image data by using the cross-sectional plane identified by the position aligning unit 17*c* (step S105), and the monitor 2 displays the ultrasound image data and the reference image data under the control of the controlling unit 19 (step S106). Subsequently, the controlling unit 19 judges whether a guide display function end request has been received (step S107).

If no end request has been received (step S107: No), the position aligning unit 17*c* judges whether the position information of the ultrasound probe 1 obtained by the obtaining unit 17*a* has changed (step S108). If the position information has not changed (step S108: No), the process returns to step S107 where the controlling unit 19 judges whether a guide display function end request has been received.

On the contrary, if the position information has changed (step S108: Yes), the position aligning unit 17*c* causes the MPR image generating unit 17*d* to re-generate reference image data, by updating the cross-sectional plane on a basis of a change amount of the position information (step S109). After that, under control of the controlling unit 19, the monitor 2 displays the ultrasound image data and the re-generated reference image data (step S110), and the process returns to step S107 where the controlling unit 19 judges whether a guide display function end request has been received.

After that, if a guide display function end request has been received (step S107: Yes), the controlling unit 19 ends the guide display function.

As explained above, in the first embodiment, it is possible to realize the guide display function that is equivalent to the conventional concurrent display function, by extracting the reference image data similar to the ultrasound image data of the subject P, while using the group of reference-purpose volume data of the subject other than the subject P. As a result, according to the first embodiment, even if no reference-purpose volume data of the subject of whom the ultrasound image was taken is available, it is possible to display the reference-purpose image for the ultrasound image. Furthermore, according to the first embodiment, because it is possible to automatically perform the position alignment processing between the pieces of image data of the mutually-different subjects, it is possible to reduce the burden on the operator.

Furthermore, according to the first embodiment, after the cross-sectional plane corresponding to the ultrasound image data currently displayed has been identified by performing the pattern matching processing, the cross-sectional plane used for extracting the reference image data from the reference volume data of the person who is not the examined subject is changed by realizing the tracking synchronization with the changes in the position information of the ultrasound probe 1. As a result, according to the first embodiment, even if the reference volume data of a person who is not the examined subject is used, it is possible to utilize the conventional position detection system in a diverse manner, and it is therefore possible to realize the guide display function at a low cost.

Furthermore, according to the first embodiment, it is possible to set the orientation of the cross-sectional plane (the cross-sectional plane orientation) by obtaining not only the imaging region, but also the scan direction of the ultrasound image data, while using the position detection system. As a result, according to the first embodiment, it is possible to improve the level of precision in the extraction of the reference image data and to shorten the processing time required by the extraction of the reference image data. Furthermore, according to the first embodiment, in addition to the setting processing to set the imaging region and the cross-sectional plane orientation, the setting processing is further performed on a basis of the information about the organ serving as the imaging region and the cross-sectional area, it is possible to further improve the level of precision in the extraction of the reference image data and to further shorten the processing time required by the extraction of the reference image data.

Second Embodiment

Figure 13:
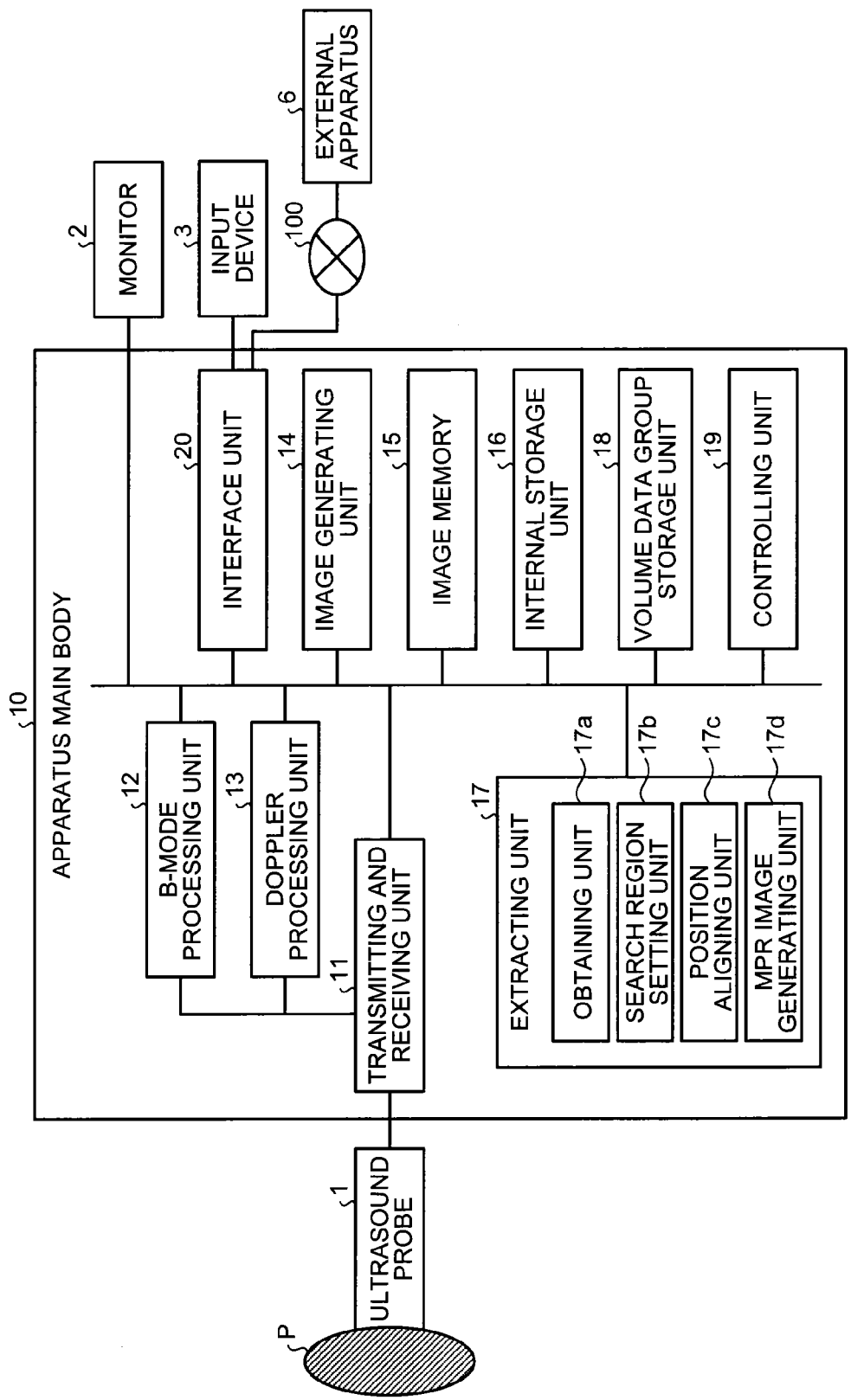
FIG. 13 is a block diagram of an exemplary configuration of an ultrasound diagnosis apparatus according to a second embodiment.

In a second embodiment, an example will be explained in which reference image data is extracted without using any position detection system. FIG. 13 is a block diagram of an exemplary configuration of an ultrasound diagnosis apparatus according to the second embodiment.

As illustrated in FIG. 13, the ultrasound diagnosis apparatus according to the second embodiment is configured by omitting the position detection system including the position sensor 4 and the transmitter 5 from the ultrasound diagnosis apparatus according to the first embodiment illustrated in FIG. 1. In this configuration, the extracting unit 17 according to the second embodiment extracts reference image data from a group of reference volume data.

First, the obtaining unit 17a according to the second embodiment obtains information about the imaging region indicated by the ultrasound image data from input information input by an operator. After that, the search region setting unit 17b according to the second embodiment sets the search region on a basis of the obtained information.

In other words, in the second embodiment, the search region is set on a basis of the input information input by the operator. The input information is, for example, information about the examined site that is conventionally specified by an operator on an examined item setting screen, as preset information about the ultrasound examination. For example, from input information such as "examined site: heart" that is specified as examination preset information, the obtaining unit 17a obtains "imaging region: chest".

Alternatively, the input information may be a body mark selected by the operator. For example, from a designation of a body mark on the liver, the obtaining unit 17a obtains "imaging region: upper abdomen".

Figure 14:
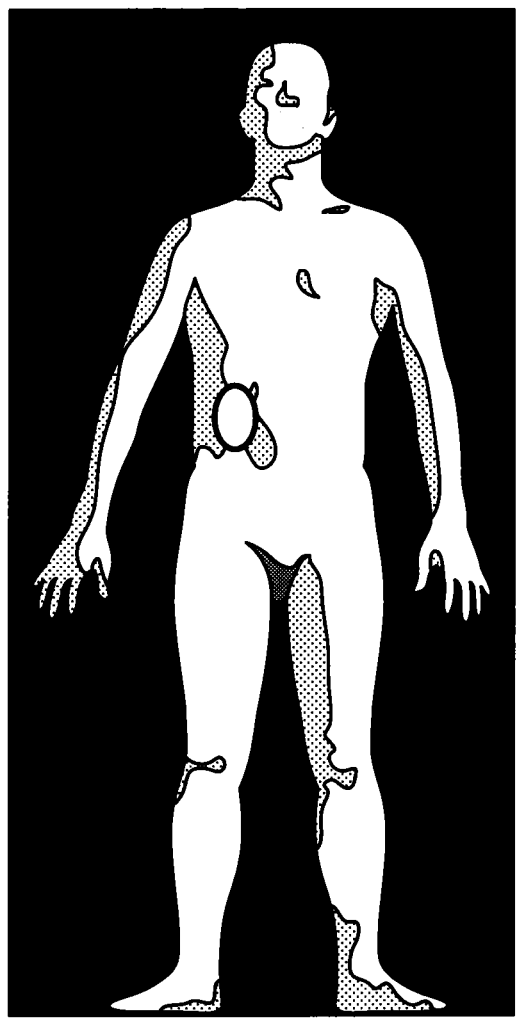
FIG. 14 is a drawing for explaining an example of a process performed by an obtaining unit according to the second embodiment.

Alternatively, it is also acceptable to display, as a GUI exclusively used for the guide display function, a "region selecting menu" from which the operator is able to select and specify an imaging region. For example, the GUI may be configured with an interface with which the operator is able to select an imaging region from a list showing various imaging regions. Alternatively, the GUI may be configured with a graphical interface as illustrated in FIG. 14. FIG. 14 is a drawing for explaining an example of a processing performed by the obtaining unit according to the second embodiment.

For example, as illustrated in FIG. 14, the controlling unit 19 causes the monitor 2 to display a human-body model drawing. After that, as illustrated in FIG. 14, for example, the operator specifies the upper abdomen shown on the left side as an imaging region, by using a mouse or the like. As a result, the obtaining unit 17a obtains "imaging region: upper abdomen". In that situation, the search region setting unit 17b according to the second embodiment narrows down the search region to the reference volume data that is kept in correspondence with "imaging region: upper abdomen", on a basis of the input information. The input information in this situation may be information about the organ serving as the imaging region. In that situation, for example, the search region setting unit 17b sets the region of the "liver" in the reference volume data kept in correspondence with "imaging region: upper abdomen", as the search region. Furthermore, in the second embodiment also, the search region setting processing based on the body information may be performed.

After that, the position aligning unit 17c identifies the position of a cross-sectional plane on which it is possible to generate reference image data similar to the ultrasound image data being displayed. Accordingly, the MPR image generating unit 17d generates the reference image data. It should be noted, however, that the search region setting unit 17b sets only the imaging region in the second embodiment. Consequently, the position aligning unit 17c according to the second embodiment performs a pattern matching processing by using a group of candidate image data obtained by cross-sectioning the reference volume data of the region including the imaging region indicated by the ultrasound image data, on cross-sectional planes in a plurality of orientations. Accordingly, the position aligning unit 17c identifies the cross-sectional plane used for generating the reference image data. The second embodiment may be configured in a manner that the search region is further narrowed down by the ultrasound scan direction information as explained in the first embodiment that is input by the operator as the information about the imaging region.

Furthermore, in the second embodiment also, the extracting unit 17 performs the processing of extracting reference image data again, in conjunction with an update of the ultrasound image data. It should be noted that, however, in the second embodiment where no position detection system is used, it is necessary to sequentially perform pattern matching processing for the purpose of identifying the cross-sectional plane that corresponds to the most up-to-date ultrasound image data, in order to move the cross-sectional plane of the reference image data in synchronization with updates of the ultrasound image data.

To realize the processing described above, for example, the position aligning unit 17c detects a feature value of the ultrasound image data being displayed and judges whether the detected feature value has changed or not. After that, when having determined that the ultrasound image data has been updated on a basis of a change in the feature value, the position aligning unit 17c performs a pattern matching processing. However, it should be noted that, if the pattern matching processing is frequently performed repeatedly, the processing load becomes heavier, and the real-time characteristics of the guide display function may be degraded as a result.

For this reason, it is desirable to configure the second embodiment in such a manner that the processing of re-extracting reference image data is performed when the operator who has determined that the ultrasound scan cross-sectional plane has been updated due to a move of the ultrasound probe 1 requests that the reference image data should be updated.

Figure 15:
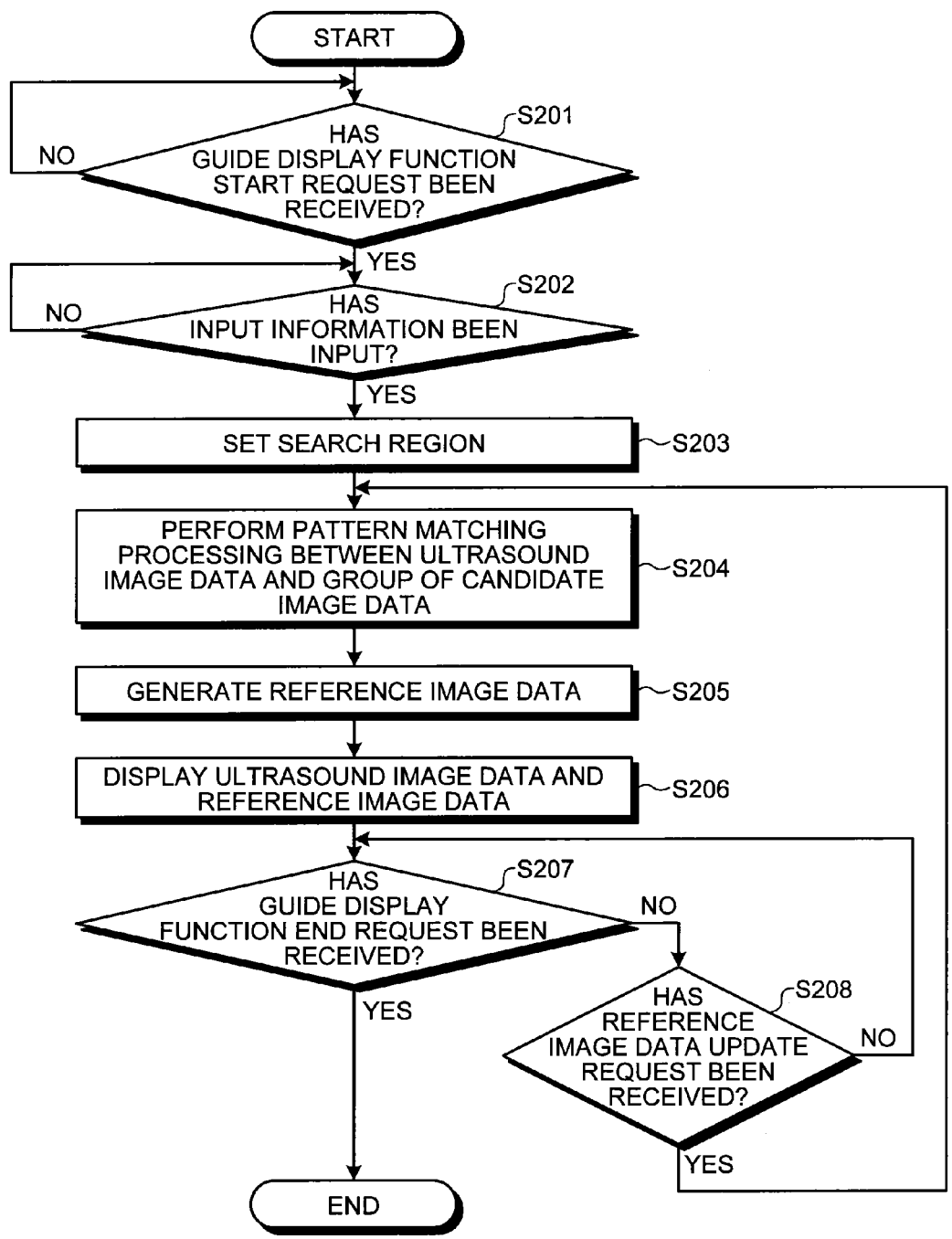
FIG. 15 is a flowchart for explaining a guide display function realized by the ultrasound diagnosis apparatus according to the second embodiment.

Next, an example of a processing in a guide display function realized by the ultrasound diagnosis apparatus according to the second embodiment will be explained, with reference to FIG. 15. FIG. 15 is a flowchart for explaining the guide display function realized by the ultrasound diagnosis apparatus according to the second embodiment. The example illustrated in FIG. 15 explains a processing that is performed after an examined site is scanned by the ultrasound probe 1. Also, the example illustrated in FIG. 15 explains a situation where the processing of re-extracting reference image data is performed in response to a request from the operator.

As illustrated in FIG. 15, the controlling unit 19 of the ultrasound diagnosis apparatus according to the second embodiment judges whether a guide display function start request has been received (step S201). If no start request has been received (step S201: No), the controlling unit 19 stands by until a start request is received.

On the contrary, if a guide display function start request has been received (step S201: Yes), the obtaining unit 17*a* judges whether input information specifying an imaging region has been input by the operator (step S202). If no input information has been input (step S202: No), the obtaining unit 17*a* stands by until input information is input.

On the contrary, if input information has been input (step S202: Yes), the obtaining unit 17*a* obtains the imaging region, and the search region setting unit 17*b* sets a search region in the group of reference volume data (step S203). After that, the position aligning unit 17*c* performs a pattern matching processing between the ultrasound image data and a group of candidate image data (step S204). The position aligning unit 17*c* selects, by performing a pattern matching processing, the piece of candidate image data having the highest level of similarity to the ultrasound image data and identifies the position of the cross-sectional plane of the selected piece of candidate image data in the reference volume data.

After that, the MPR image generating unit 17*d* generates reference image data by using the cross-sectional plane identified by the position aligning unit 17*c* (step S205), and the monitor 2 displays the ultrasound image data and the reference image data under the control of the controlling unit 19 (step S206). Subsequently, the controlling unit 19 judges whether a guide display function end request has been received (step S207).

If no end request has been received (step S207: No), the position aligning unit 17*c* judges whether a reference image data update request has been received (step S208). If no update request has been received (step S208: No), the process returns to step S207 where the controlling unit 19 judges whether a guide display function end request has been received.

On the contrary, if a reference image data update request has been received (step S208: Yes), the process returns to step S204 where a pattern matching processing is performed by using the ultrasound image data displayed at the time when the update was requested.

After that, if a guide display function end request has been received (step S207: Yes), the controlling unit 19 ends the guide display function.

As explained above, according to the second embodiment, it is possible to realize the guide display function without installing any position detection system for the ultrasound probe 1. Consequently, according to the second embodiment, it is possible to realize the guide display function at a low cost.

Third Embodiment

Figure 16:
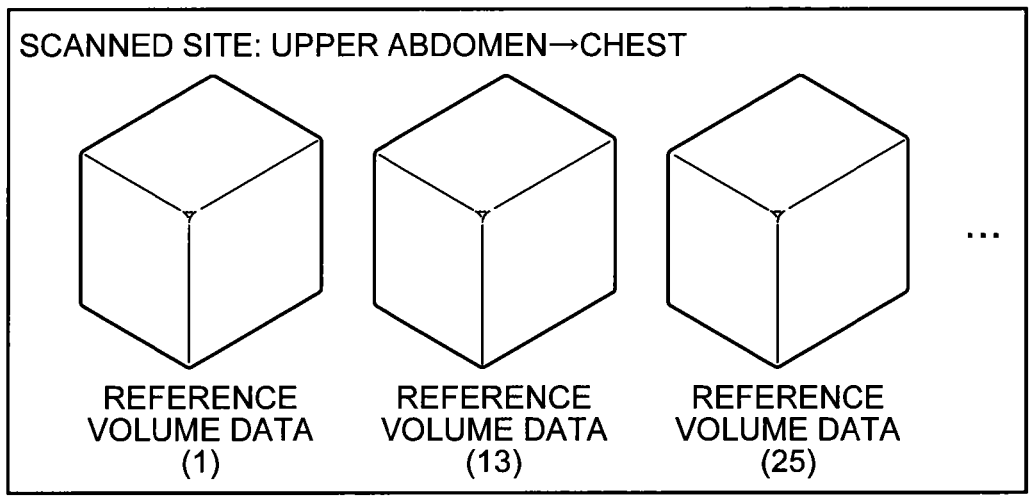
FIG. 16 is a drawing for explaining a third embodiment.

In a third embodiment, a modification example of the first embodiment in which the position information of the ultrasound probe 1 is used will be explained, with reference to FIG. 16 and so on. FIG. 16 is a drawing for explaining the third embodiment.

An ultrasound diagnosis apparatus according to the third embodiment is configured in the same manner as the ultrasound diagnosis apparatus according to the first embodiment shown in FIG. 1. In other words, like in the first embodiment, the obtaining unit 17*a* according to the third embodiment obtains the position information of the ultrasound probe 1 from the position sensor 4. After that, the search region setting unit 17*b* according to the third embodiment sets a search region where reference image data is searched for from a group of reference volume data, on a basis of the position information of the ultrasound probe 1. After that, the position aligning unit 17*c* according to the third embodiment selects, by performing a pattern matching processing, the piece of reference volume data including the candidate image data that is most similar to the ultrasound image data and identifies a cross-sectional plane used for generating the reference image data from the selected piece of reference volume data.

After that, in the third embodiment also, the cross-sectional plane used for extracting reference image data from the reference volume data is changed by realizing a tracking synchronization with a change in the position information of the ultrasound probe 1, the reference volume data corresponding to the selected region set by the search region setting unit 17*b* and having been selected by the position aligning unit 17*c*.

It should be noted, however, that the scan region of the ultrasound probe 1 may, in some situations, move outside of the search region that is set initially. To cope with this situation, when the extracting unit 17 according to the third embodiment has determined that an ultrasound scan region has moved outside of the search region, as being judged from a change amount of the position information of the ultrasound probe 1, the extracting unit 17 updates the search region in accordance with the change amount. After that, the extracting unit 17 according to the third embodiment re-extracts reference image data, from the group of reference volume data in the updated search region.

For example, the search region setting unit 17*b* according to the third embodiment calculates a change amount of the position information of the ultrasound probe 1 obtained by the obtaining unit 17*a*. The change amount is represented by a moving distance and a moving direction of the ultrasound probe 1. While the tracking synchronization is being performed, the search region setting unit 17*b* constantly calculates change amounts. Furthermore, for example, the search region setting unit 17*b* judges whether the scanned site is positioned at the "upper abdomen", on a basis of the calculated change amounts.

For example, let us discuss a situation where, as illustrated in FIG. 16, the search region setting unit 17*b* has detected, on a basis of a change amount of the position information, that the scanned site has moved outside of the "upper abdomen" region and that the scanned site has moved from the "upper abdomen" to the "chest". In that situation, the search region setting unit 17*b* changes the reference volume data from which reference image data is to be extracted, from the group of reference volume data corresponding to "imaging region: upper abdomen", to the group of reference volume data corresponding to "imaging region: chest". For example, as illustrated in FIG. 16, the search region setting unit 17*b* selects "reference volume data (1), reference volume data (13), reference volume data (25) . . . " from the group of reference volume data. After that, the search region setting unit 17*b* also sets orientations of the cross-sectional planes for "reference volume data (1), reference volume data (13), reference volume data (25) . . . ". The search region setting processing that is performed when the ultrasound scan region has moved outside of the search region may include not only the processing of setting the imaging region and the cross-sectional plane orientations, but also any of the other setting processing explained in the first embodiment.

After that, the position aligning unit 17*c* and the MPR image generating unit 17*d* perform the processing explained in the first embodiment while using the ultrasound image data that is currently displayed and "reference volume data (1), reference volume data (13), reference volume data (25) . . . ".

Figure 17:
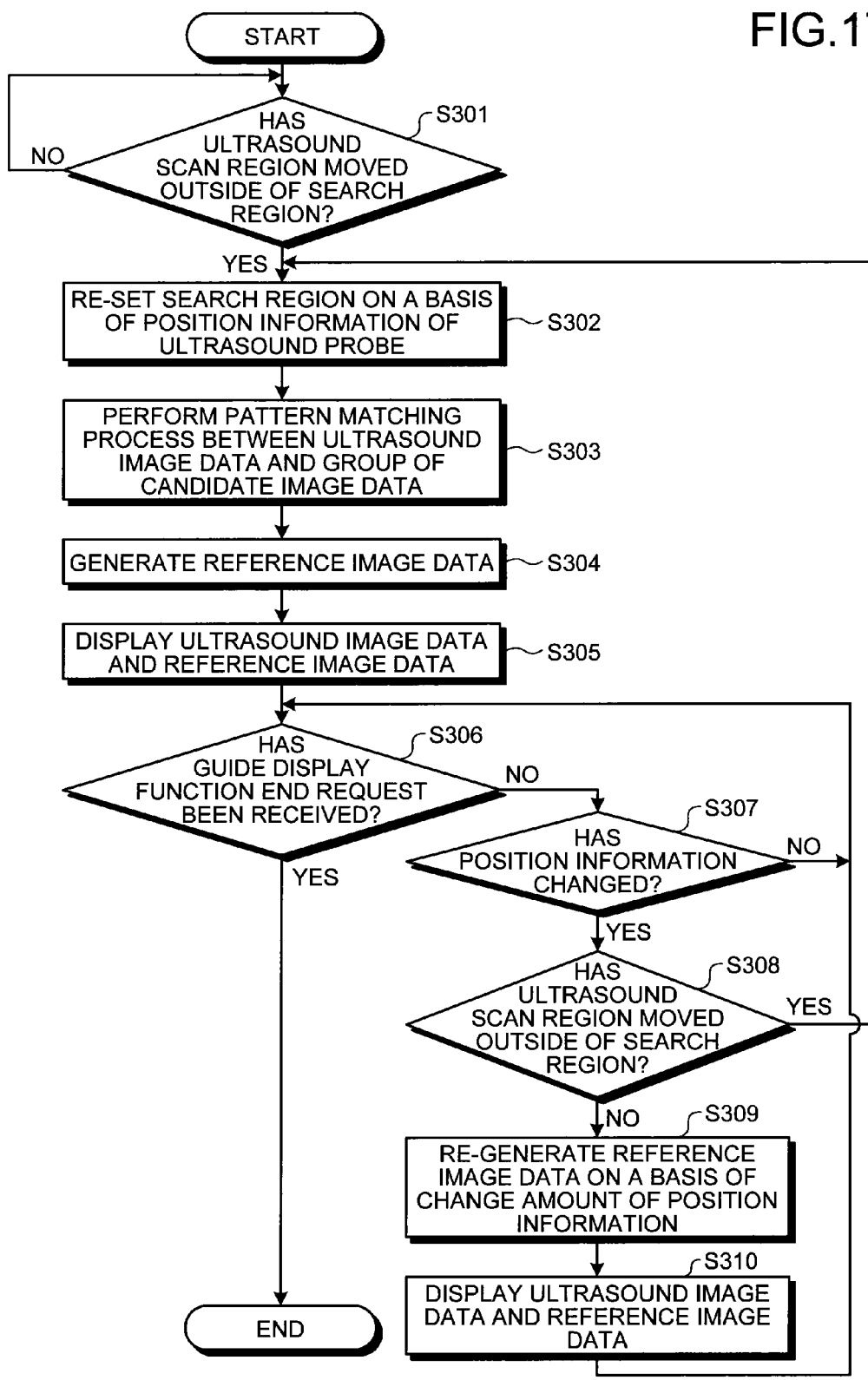
FIG. 17 is a flowchart for explaining a guide display function realized by an ultrasound diagnosis apparatus according to the third embodiment.

Next, an example of a processing in a guide display function realized by the ultrasound diagnosis apparatus according to the third embodiment will be explained, with reference to FIG. 17. FIG. 17 is a flowchart for explaining the guide display function realized by the ultrasound diagnosis apparatus according to the third embodiment. FIG. 17 illustrates an example of a processing that is performed after the tracking synchronization based on the position information explained in the first embodiment has been started.

As illustrated in FIG. 17, the search region setting unit 17*b* of the ultrasound diagnosis apparatus according to the third embodiment judges whether the ultrasound scan region has moved outside of the search region (step S301). If the ultrasound scan region has not moved outside of the search region (step S301: No), the tracking synchronization is continued. Furthermore, the search region setting unit 17*b* continues to judge whether the ultrasound scan region has moved outside of the search region.

On the contrary, if the ultrasound scan region has moved outside of the search region (step S301: Yes), the search region setting unit 17*b* re-sets a search region for the group of reference volume data, on a basis of the position information of the ultrasound probe 1 (step S302). More specifically, the search region setting unit 17*b* re-selects reference volume data and re-sets a cross-sectional plane corresponding to the scan direction.

After that, the position aligning unit 17*c* performs a pattern matching processing between the ultrasound image data and a group of candidate image data (step S303). The group of candidate image data is a group of MPR image data in the search region that was re-set. The position aligning unit 17*c* selects, by performing a pattern matching processing, the piece of candidate image data having the highest level of similarity to the ultrasound image data and identifies the position of the cross-sectional plane of the selected piece of candidate image data in the reference volume data.

After that, the MPR image generating unit 17*d* generates reference image data by using the cross-sectional plane identified by the position aligning unit 17*c* (step S304), and the monitor 2 displays the ultrasound image data and the reference image data under the control of the controlling unit 19 (step S305). Subsequently, the controlling unit 19 judges whether a guide display function end request has been received (step S306).

If no end request has been received (step S306: No), the position aligning unit 17*c* judges whether the position information of the ultrasound probe 1 obtained by the obtaining unit 17*a* has changed (step S307). If the position information has not changed (step S307: No), the process returns to step S306 where the controlling unit 19 judges whether a guide display function end request has been received.

On the contrary, if the position information has changed (step S307: Yes), the search region setting unit 17*b* judges again whether the ultrasound scan region has moved outside of the search region (step S308). If the ultrasound scan region has moved outside of the search region (step S308: Yes), the process returns to step S302 where the search region setting unit 17*b* re-sets a search region.

On the contrary, if the ultrasound scan region is positioned inside the search region (step S308: No), the position aligning unit 17*c* causes the MPR image generating unit 17*d* to re-generate reference image data, by updating the cross-sectional plane on a basis of a change amount of the position information (step S309). After that, under control of the controlling unit 19, the monitor 2 displays the ultrasound image data and the re-generated reference image data (step S310), and the process returns to step S306 where the controlling unit 19 judges whether a guide display function end request has been received.

After that, if a guide display function end request has been received (step S306: Yes), the controlling unit 19 ends the guide display function.

The third embodiment may be configured so that, if it has been detected that the scanned site has moved outside of the search region that was set, the monitor 2 is caused to display a message indicating that the scanned site has moved outside of the search region. Furthermore, the third embodiment may be configured so that the processing of re-extracting reference image data is performed only if the operator who has been informed that the scanned site has moved outside of the search region inputs information permitting a change of the search region and a re-extraction processing of reference image data.

When the guide display function is used, because the reference image data is not image data of the examined subject, it is necessary to re-select the reference volume data from which candidate image data is generated, every time the scanned site is changed. However, as explained above, according to the third embodiment, the processing of re-selecting the reference volume data is performed if it has been detected that the scanned site has moved outside of the search region. Consequently, according to the third embodiment, even if the scanned site is significantly changed, it is possible to display the reference image data similar to the ultrasound image data.

Fourth Embodiment

Figure 18:
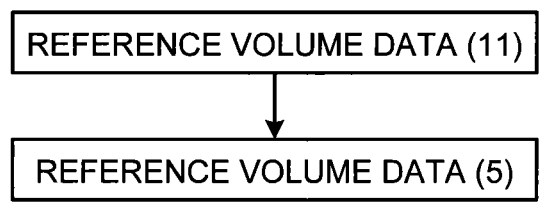
FIG. 18 is a drawing for explaining a fourth embodiment.

In a fourth embodiment, a processing that is performed when the operator has determined that reference image data and ultrasound image data are dissimilar to each other will be explained, with reference to FIG. 18 and so on. FIG. 18 is a drawing for explaining the fourth embodiment.

Functions of an ultrasound diagnosis apparatus according to the fourth embodiment are applicable to any of the ultrasound diagnosis apparatuses according to the first to the third embodiments. In the following sections, an example will be explained in which the ultrasound diagnosis apparatus according to the fourth embodiment is configured in the same manner as the ultrasound diagnosis apparatus according to the first embodiment.

For example, the operator refers to the reference image data displayed at step S106 of the flowchart shown in FIG. 12. In this situation, if the operator has determined that the morphology of the tissue rendered in the reference image data is dissimilar to the morphology of the tissue rendered in the ultrasound image data, the operator inputs a reference image data re-extraction request.

When having received a re-extraction request from an operator who has referred to the ultrasound image data and the reference image data displayed on the monitor 2, the extracting unit 17 according to the fourth embodiment re-extracts reference image data serving as a next candidate from the group of volume data. For example, as illustrated in FIG. 18, the position aligning unit 17c according to the fourth embodiment changes the reference volume data on which the position alignment processing is to be performed, from reference volume data (11) including the piece of candidate image data having the highest level of similarity, to reference volume data (5) including the piece of candidate image data having the second highest level of similarity.

After that, the position aligning unit 17c according to the fourth embodiment identifies the cross-sectional plane in reference volume data (5).

It is also acceptable to configure the position aligning unit 17c according to the fourth embodiment so as to perform, again, a position alignment processing (a pattern matching processing) between the pieces of reference volume data in the search region and the ultrasound image data. In that situation, for example, the position aligning unit 17c according to the fourth embodiment performs the pattern matching processing again, after changing the implemented method from a cross-correlation method to an auto-correlation method.

Figure 19:
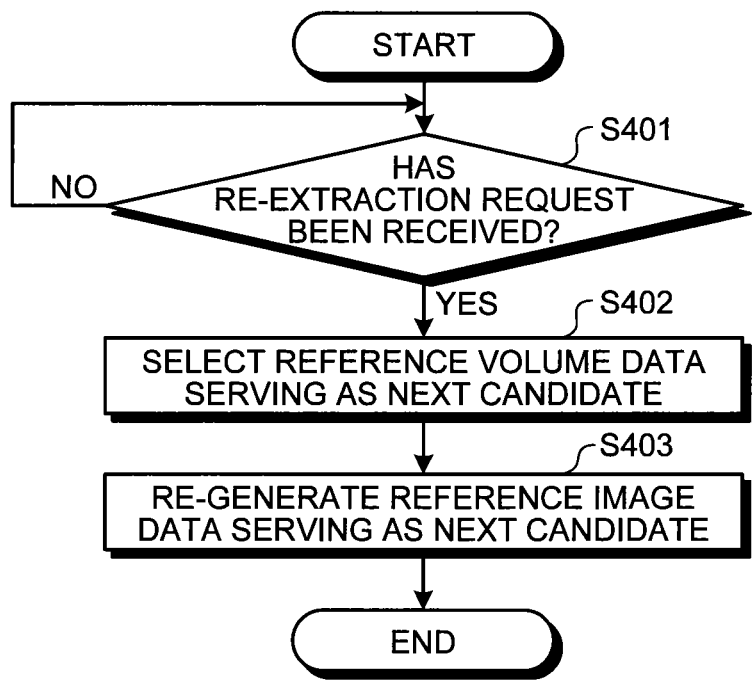
FIG. 19 is a flowchart for explaining a guide display function realized by an ultrasound diagnosis apparatus according to the fourth embodiment.

Next, an example of a processing in a guide display function realized by the ultrasound diagnosis apparatus according to the fourth embodiment will be explained with reference to FIG. 19. FIG. 19 is a flowchart for explaining the guide display function realized by the ultrasound diagnosis apparatus according to the fourth embodiment.

As shown in FIG. 19, the controlling unit 19 of the ultrasound diagnosis apparatus according to the fourth embodiment judges whether a reference image data re-extraction request has been received from the operator (step S401). If no re-extraction request has been received (step S401: No), the controlling unit 19 stands by until a re-extraction request is received, without sending instructions to the position aligning unit 17c.

On the contrary, if a re-extraction request has been received (step S401: Yes), the position aligning unit 17c selects a piece of reference volume data serving as the next candidate, according to an instruction from the controlling unit 19 (step S402). After that, by using a cross-sectional plane identified by the position aligning unit 17c as a result of a pattern matching processing performed between the piece of reference volume data serving as the next candidate and the ultrasound image data, the MPR image generating unit 17d re-generates reference image data serving as the next candidate (step S403), and the processing is ended. The reference image data generated at step S403 is displayed on the monitor 2 again.

As explained above, according to the fourth embodiment, when the operator has determined that the matching property between the ultrasound image data and the reference image data is not satisfactory, the reference image data re-extraction processing is performed. Consequently, according to the fourth embodiment, by repeatedly performing the re-extraction processing, it is possible to display such reference image data that is intuitively recognized by the operator as having a satisfactory matching property.

Fifth Embodiment

Figure 20:
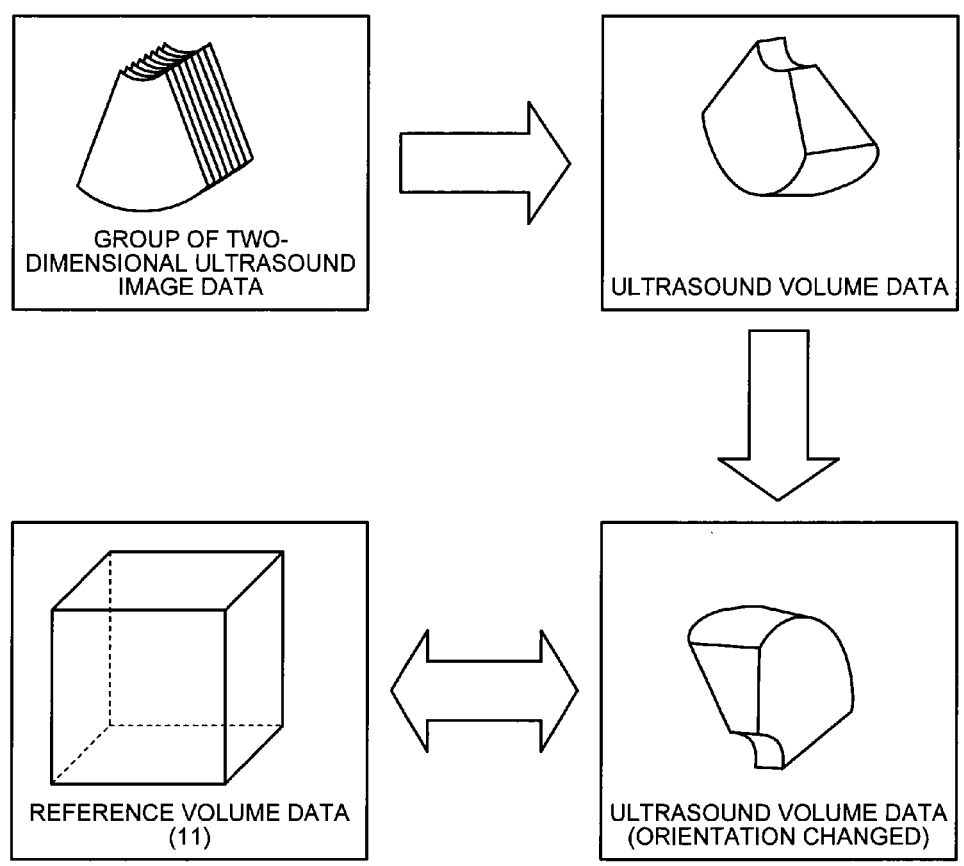
FIG. 20 is a drawing for explaining a fifth embodiment.

In a fifth embodiment, an example will be explained in which the position aligning unit 17c performs the pattern matching processing between pieces of three-dimensional image data, with reference to FIG. 20 and so on. FIG. 20 is a drawing for explaining the fifth embodiment.

The level of precision of a position alignment processing is higher when performed between pieces of volume data than when performed between pieces of two-dimensional image data. For this reason, an ultrasound diagnosis apparatus according to the fifth embodiment is obtained by adding the function described below, to the ultrasound diagnosis apparatus according to the first or the third embodiment that obtains the position information of the ultrasound probe 1.

First, the operator acquires a group of two-dimensional ultrasound image data on which a pattern matching processing is to be performed. The group of two-dimensional ultrasound image data illustrated in the top left section of FIG. 20 is acquired by sliding the ultrasound probe 1, which is a 1D array probe, while arranging the ultrasound probe 1 to abut against the body surface of the subject P.

The obtaining unit 17a obtains position information of the ultrasound probe 1 corresponding to the time when the group of two-dimensional ultrasound image data was acquired. The search region setting unit 17b sets a search region on a basis of the position information of the ultrasound probe 1 corresponding to the time when the group of two-dimensional ultrasound image data was acquired.

After that, the position aligning unit 17c arranges the group of two-dimensional ultrasound image data into a three-dimensional space, on a basis of the position information of the ultrasound probe 1 corresponding to the time when the group of two-dimensional ultrasound image data was acquired. Accordingly, as illustrated in the top right section of FIG. 20, the position aligning unit 17c re-constructs ultrasound volume data from the group of two-dimensional ultrasound image data.

After that, for example, as illustrated in FIG. 20, the position aligning unit 17c performs a pattern matching processing between reference volume data (11) selected as reference volume data in the search region and the ultrasound volume data. In that situation, for example, as shown in the bottom right section of FIG. 20, the position aligning unit 17c performs the pattern matching processing with reference volume data (11), after changing the orientation of the ultrasound volume data, on a basis of the position information (three-dimensional scan direction information).

It is possible to realize a similarity level calculating processing performed in the fifth embodiment, by extending the processing explained in the first embodiment to a three-dimensional system.

After that, the position aligning unit 17c selects the piece of reference volume data having the highest level of similarity to the ultrasound volume data and identifies a three-dimensional region within the selected piece of reference volume data that corresponds to the ultrasound volume data. Subsequently, in the selected piece of reference volume data, the position aligning unit 17c identifies the position of the cross-sectional plane corresponding to the piece of two-dimensional ultrasound image data (e.g., the piece of two-dimensional ultrasound image data in the last frame) specified out of the group of two-dimensional ultrasound image data.

Accordingly, the MPR image generating unit 17d generates reference image data that is similar to the two-dimensional ultrasound image data in the last frame.

Figure 21:
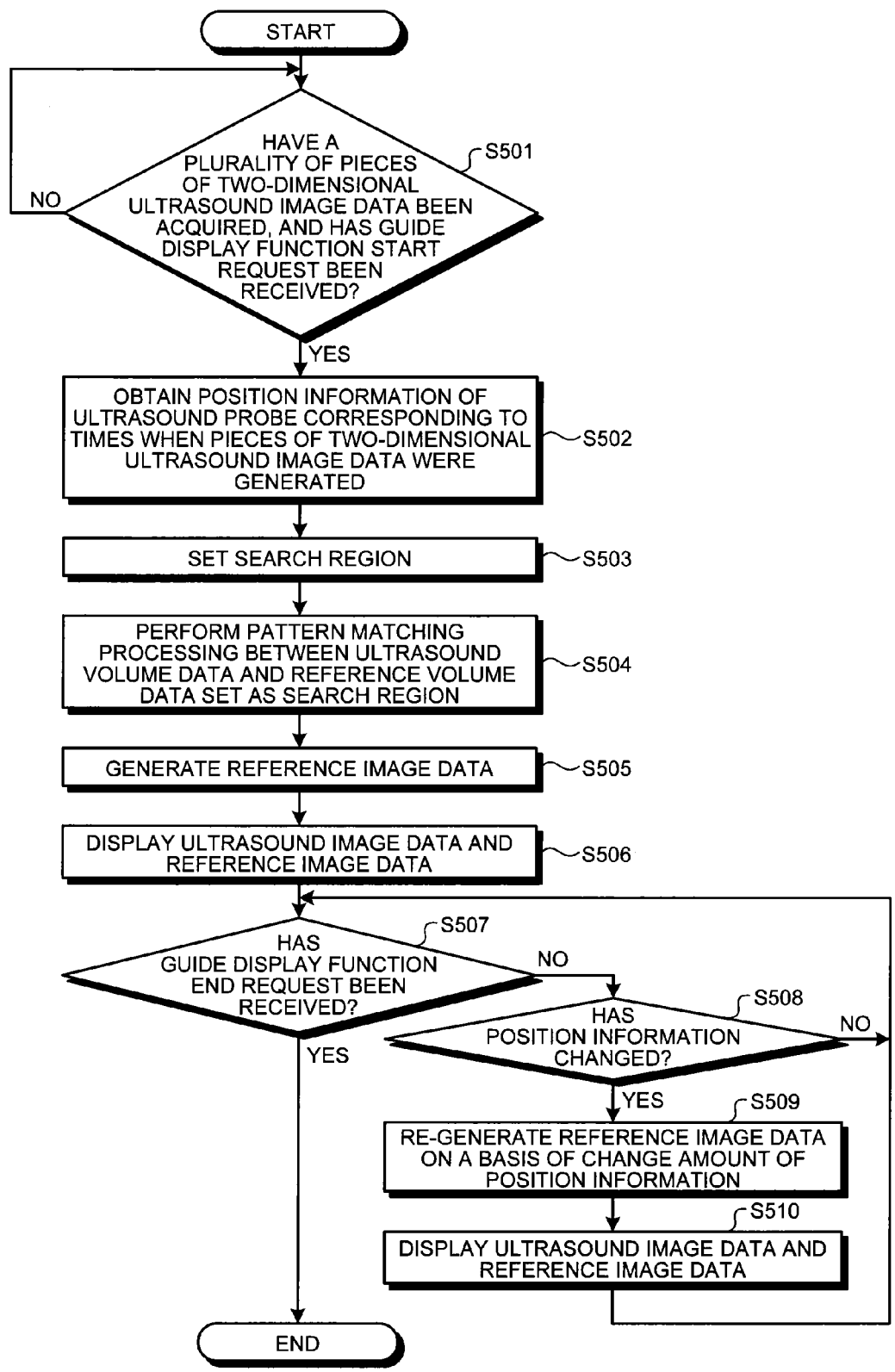
FIG. 21 is a flowchart for explaining a guide display function realized by an ultrasound diagnosis apparatus according to the fifth embodiment.

Next, an example of a processing in a guide display function realized by the ultrasound diagnosis apparatus according to the fifth embodiment will be explained, with reference to FIG. 21. FIG. 21 is a flowchart for explaining the guide display function realized by the ultrasound diagnosis apparatus according to the fifth embodiment. The example illustrated in FIG. 21 explains a processing that is performed after the registration of the initial information for realizing the guide display function has been completed, and also, the ultrasound probe 1 has been moved from the initial position so as to three-dimensionally scan an examined site.

As shown in FIG. 21, the controlling unit 19 of the ultrasound diagnosis apparatus according to the fifth embodiment judges whether a plurality of piece of two-dimensional ultrasound image data have been acquired, and a guide display function start request has been received (step S501). If no start request has been received (step S501: No), the controlling unit 19 stands by until a start request is received.

On the contrary, if a guide display function start request has been received (step S501: Yes), the obtaining unit 17a obtains the position information of the ultrasound probe 1 corresponding to the times when the pieces of two-dimensional image data were generated (step S502), and the search region setting unit 17b sets a search region in the group of reference volume data (step S503). After that, the position aligning unit 17c reconstructs ultrasound volume data from the two-dimensional ultrasound image data and performs a pattern matching processing between the ultrasound volume data and the reference volume data set as the search region (step S504). Accordingly, the position aligning unit 17c selects, by performing a pattern matching processing, the piece of reference volume data having the highest level of similarity to the ultrasound image volume data and identifies a three-dimensional region within the selected piece of reference volume data that corresponds to the ultrasound volume data. Furthermore, in the selected piece of reference volume data, the position aligning unit 17c identifies the position of the cross-sectional plane corresponding to the two-dimensional ultrasound image data specified out of the group of two-dimensional ultrasound image data.

After that, the MPR image generating unit 17d generates reference image data by using the cross-sectional plane identified by the position aligning unit 17c (step S505), and the monitor 2 displays the ultrasound image data and the reference image data under the control of the controlling unit 19 (step S506). Subsequently, the controlling unit 19 judges whether a guide display function end request has been received (step S507).

If no end request has been received (step S507: No), the position aligning unit 17c judges whether the position information of the ultrasound probe 1 obtained by the obtaining unit 17a has changed (step S508). If the position information has not changed (step S508: No), the process returns to step S507 where the controlling unit 19 judges whether a guide display function end request has been received.

On the contrary, if the position information has changed (step S508: Yes), the position aligning unit 17c causes the MPR image generating unit 17d to re-generate reference image data, by updating the cross-sectional plane on a basis of a change amount of the position information (step S509). After that, under control of the controlling unit 19, the monitor 2 displays the ultrasound image data and the re-generated reference image data (step S510), and the process returns to step S507 where the controlling unit 19 judges whether a guide display function end request has been received.

After that, if a guide display function end request has been received (step S507: Yes), the controlling unit 19 ends the guide display function.

The fifth embodiment is also applicable to a situation where a mechanical 4D probe or a 2D array probe is used as the ultrasound probe 1 to reconstruct the ultrasound volume data. Furthermore, it is acceptable to configure the fifth embodiment, also, so that the out-of-region detecting processing explained in the third embodiment is performed.

As explained above, according to the fifth embodiment, by performing the pattern matching processing between the pieces of three-dimensional image data, it is possible to extract the reference image data having a high level of similarity with a high level of precision.

It is acceptable to configure any of the first to the fifth embodiments described above in such a manner that, when performing the pattern matching processing between the ultrasound image data and the group of volume data in the search region, the position aligning unit 17c sets a region within the ultrasound image data that serves as a comparison target. In an example, the operator sets a region within the ultrasound image data that is to be used for calculating a level of similarity to perform the position alignment processing. For example, by using the input device 3, the operator selects only an image region having clear morphological information as the region to be used for comparing the levels of similarity, while excluding noise regions and regions having unsatisfactory image quality. The position aligning unit 17c performs a pattern matching processing by using the set region received by the input device 3. As a result, it is possible to further reduce the load in the position alignment processing. In one example, the region within the ultrasound image data to be used for comparing the levels of similarity may be set by, for example, the position aligning unit 17c that detects the noise regions and the regions having unsatisfactory image quality. Alternatively, the region within the ultrasound image data to be used for comparing the levels of similarity may be set by the controlling unit 19 that automatically detects a region having the largest contrast value as an image region having clear morphological information.

Furthermore, in the first to the fifth embodiments described above, the example is explained in which the reference volume data serving as the volume data from which the reference image data is extracted is the volume data of the subject other than the subject P. However, it is also acceptable to configure any of the first to the fifth embodiments described above in such a manner that the volume data from which the reference image data is extracted is volume data that imitates a human body. For example, the reference volume data may be extracted from a group of volume data of a human body that is artificially created. The group of artificial volume data is represented by, for example, a plurality of piece of volume data that are created in correspondence with various types of body information, while using a publicly-known computer graphic technique. Alternatively, the group of artificial volume data may be a group of volume data obtained by taking images, with the use of a medical image diagnosis apparatus (e.g., an ultrasound diagnosis apparatus, an X-ray CT apparatus, an MRI apparatus, or the like), of a plurality of phantoms created so as to precisely imitate internal tissues of the human body on a basis of various types of body information. With this arrangement also, it is possible to display a reference-purpose image for the ultrasound image, even if no reference-purpose volume data of the subject of whom the ultrasound image was taken is available. Furthermore, it is also acceptable to extract the reference image data from a group of volume data which is a mixture of both a group of volume data of a subject other than the subject P and a group of volume data of the human body.

Furthermore, it is also acceptable to extract the reference image data from a group of volume data of an arbitrary subject (including the subject P) taken by a medical image diagnosis apparatus. As explained above, according to the image processing methods explained in the first to the fifth embodiments, the search region is set (i.e., the search region is narrowed down) on a basis of the information about the imaging region. Thus, by using any of the image processing methods explained in the first to the fifth embodiments, it is possible to shorten the processing time required by the reference image data extracting processing realized by performing the position alignment processing.

Accordingly, by using any of the image processing methods explained in the first to the fifth embodiments, it is possible to promptly extract the reference image data corresponding to the ultrasound image data displayed on the monitor 2, also from a group of volume data that was obtained in the past by taking images of the subject P who is the image taking target of the ultrasound image data. For example, by using any of the image processing methods described above, it is possible to promptly extract the reference image data corresponding to the ultrasound image data of the subject P displayed on the monitor 2, also from a group of ultrasound volume data, a group of X-ray CT volume data, or a group of MRI volume data that was obtained in the past by taking images of the subject P.

In other words, for the purpose of promptly extracting and displaying the reference image data, any of the image processing methods explained in the first to the fifth embodiment may be implemented while the volume data group storage unit 18 has stored therein at least one of the following groups of volume data: "a group of volume data obtained by taking images of a plurality of subjects other than the subject P by using various types of medical image diagnosis apparatuses"; "a group of volume data that imitates the human body"; and "a group of volume data obtained by taking images of the subject P by using various types of medial image diagnosis apparatuses".

Furthermore, the constituent elements of the apparatuses shown in the drawings to explain the first to the fifth embodiments are based on functional concepts. Thus, it is not necessary to physically configure the elements as indicated in the drawings. In other words, the specific mode of distribution and integration of the apparatuses is not limited to the ones shown in the drawings. It is acceptable to functionally or physically distribute or integrate all or a part of the apparatuses in any arbitrary units, depending on various loads and the status of use. Furthermore, all or an arbitrary part of the processing functions performed by the apparatuses may be realized by a Central Processing Unit (CPU) and a computer program that is analyzed and executed by the CPU or may be realized as hardware using wired logic.

Furthermore, the image processing methods described in the first to the fifth embodiments may be realized by causing a computer such as a personal computer or a workstation to execute an image processing computer program (hereinafter, the "image processing program") prepared in advance. The image processing program may be distributed via a network such as the Internet. Furthermore, it is also possible to record the image processing program onto a computer-readable non-transitory recording medium such as a hard disk, a flexible disk (FD), a Compact Disc Read-Only Memory (CD-ROM), a Magneto-optical (MO) disk, a Digital Versatile Disc (DVD), or a flash memory such as a Universal Serial Bus (USB) memory or a Secure Digital (SD) card memory, so that a computer is able to read the image processing program from the non-transitory recording medium and to execute the read image processing program.

As explained above, according to an aspect of the first to the fifth embodiments, it is possible to display the reference-purpose image for the ultrasound image, even if no reference-purpose volume data of the subject of whom the ultrasound image was taken is available.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus comprising:
   circuitry configured to:
      extract, from a group of volume data, reference image data corresponding to ultrasound image data of a first subject displayed on a display; and
      cause the display to display the ultrasound image data and the reference image data, wherein
      the circuitry is configured to obtain information about an imaging region indicated by the ultrasound image data displayed on the display, and set a search region for searching the reference image data from the group of volume data based on the obtained information, the group of volume data being at least one of a first group of volume data of a second subject that is other than the first subject and a second group of volume data that imitates a human body.

2. The ultrasound diagnosis apparatus according to claim 1, wherein the group of volume data from which the reference image data is extracted is the first group of volume data of the second subject taken by a medical image diagnosis apparatus.

3. The ultrasound diagnosis apparatus according to claim 1, wherein the group of volume data from which the reference image data is extracted is the first group of volume data of the second subject taken by a medical image diagnosis apparatus of a type that is other than ultrasound diagnosis apparatuses.

4. The ultrasound diagnosis apparatus according to claim 1, wherein the circuitry is configured to obtain the information about the imaging region based on position information of an ultrasound probe corresponding to a time when the ultrasound image data was generated.

5. The ultrasound diagnosis apparatus according to claim 4, wherein, as a search region setting processing, the circuitry is configured to set a cross-sectional plane orientation and a cross-sectional area used for searching for the reference image data from pieces of the group of volume data based on the position information of the ultrasound probe and field-of-vision area information of the ultrasound image data.

6. The ultrasound diagnosis apparatus according to claim 4, wherein, when an ultrasound scan region has moved outside of the search region as being judged from a change amount of the position information of the ultrasound probe, the circuitry is configured to update the search region in accordance with the change amount, and extract another reference image data.

7. The ultrasound diagnosis apparatus according to claim 1, wherein the circuitry is configured to obtain the information about the imaging region indicated by the ultrasound image data from input information input by an operator, and set the search region based on the obtained information.

8. The ultrasound diagnosis apparatus according to claim 1, wherein the circuitry is configured to extract the reference image data by aligning positions of the ultrasound image data and the group of volume data in the search region through a pattern matching processing.

9. The ultrasound diagnosis apparatus according to claim 8, wherein the circuitry is configured to perform the pattern matching processing between pieces of two-dimensional image data.

10. The ultrasound diagnosis apparatus according to claim 8, wherein the circuitry is configured to perform the pattern matching processing between pieces of three-dimensional image data.

11. The ultrasound diagnosis apparatus according to claim 8, wherein, when performing the pattern matching processing between the ultrasound image data and the group of volume data in the search region, the circuitry is configured to set a region within the ultrasound image data that serves as a comparison target.

12. The ultrasound diagnosis apparatus according to claim 1, wherein, in conjunction with an update of the ultrasound image data, the circuitry is configured to perform a processing of extracting another reference image data.

13. The ultrasound diagnosis apparatus according to claim 1, wherein, when having received a re-extraction request from an operator who has referred to the ultrasound image data and the reference image data displayed on the display, the circuitry is configured to extract another reference image data serving as a next candidate from the group of volume data.

14. An image processing method comprising:
extracting, using circuitry from a group of volume data, reference image data corresponding to ultrasound image data of a first subject displayed on a display;
causing, using the circuitry, the display to display the ultrasound image data and the reference image data;
obtaining, using the circuitry, information about an imaging region indicated by the ultrasound image data displayed on the display; and
setting, using the circuitry, a search region for searching the reference image data from the group of volume data based on the obtained information, the group of volume data being at least one of a first group of volume data of a second subject that is other than the first subject and a second group of volume data that imitates a human body.

* * * * *